(12) United States Patent
Fujisaki et al.

(10) Patent No.: US 9,517,071 B2
(45) Date of Patent: Dec. 13, 2016

(54) TISSUE LIGATING DEVICE

(71) Applicant: OLYMPUS CORPORATION, Tokyo (JP)

(72) Inventors: Ken Fujisaki, Sagamihara (JP); Takumi Isoda, Tokyo (JP); Hirotaka Namiki, Tokorozawa (JP)

(73) Assignee: OLYMPUS CORPORATION, Tokyo (JP)

( * ) Notice: Subject to any disclaimer, the term of this patent is extended or adjusted under 35 U.S.C. 154(b) by 129 days.

(21) Appl. No.: 14/169,792

(22) Filed: Jan. 31, 2014

(65) Prior Publication Data
US 2014/0148824 A1    May 29, 2014

Related U.S. Application Data

(63) Continuation of application No. PCT/JP2012/078553, filed on Oct. 30, 2012.

(30) Foreign Application Priority Data

Oct. 31, 2011 (JP) ................................. 2011-239731
Oct. 31, 2011 (JP) ................................. 2011-239732

(51) Int. Cl.
*A61B 17/12* (2006.01)
*A61B 17/06* (2006.01)
(Continued)

(52) U.S. Cl.
CPC ..... *A61B 17/12009* (2013.01); *A61B 17/0401* (2013.01); *A61B 17/0485* (2013.01);
(Continued)

(58) Field of Classification Search
CPC ............ A61B 17/0401; A61B 17/0485; A61B 17/06166; A61B 17/12009; A61B 17/12013; A61B 2017/0446; A61B 2017/0464; A61B 2017/0618; A61B 2017/12018
See application file for complete search history.

(56) References Cited

U.S. PATENT DOCUMENTS 3,910,281 A * 10/1975 Kletschka .......... A61B 17/0401 24/18
4,069,825 A * 1/1978 Akiyama ........... A61B 17/0467 606/138
(Continued)

FOREIGN PATENT DOCUMENTS

FR    2717065 A1    9/1995
JP    08-140982 A    6/1996
(Continued)

OTHER PUBLICATIONS

International Search Report dated Jan. 29, 2013 issued in PCT/JP2012/078553.

*Primary Examiner* — Ryan J Severson
(74) *Attorney, Agent, or Firm* — Scully, Scott, Murphy & Presser, P.C.

(57) ABSTRACT

A tissue ligating device for ligating a tissue includes a suture having an elastic restoring force, and a hook-shaped member including a groove portion, connected to a first end of the suture, and disposed in a direction along a derivation direction of the suture and in a direction opposite to the derivation direction of the suture with respect to the first end of the suture.

19 Claims, 39 Drawing Sheets

(51) Int. Cl.
  *A61B 17/04*    (2006.01)
  *A61B 17/00*    (2006.01)
(52) U.S. Cl.
  CPC .............. *A61B 2017/00004* (2013.01); *A61B 2017/0446* (2013.01); *A61B 2017/0464* (2013.01); *A61B 2017/0618* (2013.01)

(56) References Cited

U.S. PATENT DOCUMENTS

| | | | | |
|---|---|---|---|---|
| 4,950,285 A * | 8/1990 | Wilk | ...................... | A61B 17/06 24/16 PB |
| 5,037,433 A * | 8/1991 | Wilk | .................. | A61B 17/0469 606/139 |
| 5,074,874 A * | 12/1991 | Yoon | .................. | A61B 17/0469 606/139 |
| 5,312,436 A * | 5/1994 | Coffey | ............... | A61B 17/0469 606/224 |
| 5,403,346 A * | 4/1995 | Loeser | ................... | A61B 17/06 606/228 |
| 5,665,109 A * | 9/1997 | Yoon | .................. | A61B 17/0469 606/139 |
| 5,683,417 A * | 11/1997 | Cooper | .................. | A61B 17/04 606/223 |
| 5,810,853 A * | 9/1998 | Yoon | .................. | A61B 17/0487 606/151 |
| 5,879,371 A * | 3/1999 | Gardiner | ............ | A61B 17/0469 606/144 |
| 5,972,024 A * | 10/1999 | Northrup, III | ... | A61B 17/06166 606/151 |
| 6,607,541 B1 * | 8/2003 | Gardiner | ................ | A61B 17/06 606/151 |
| 6,641,593 B1 * | 11/2003 | Schaller | ............... | A61B 17/083 606/157 |
| 7,862,584 B2 * | 1/2011 | Lyons | ................ | A61B 17/0487 606/232 |
| 8,109,968 B2 * | 2/2012 | Ashley | ............... | A61B 17/0487 24/130 |
| 8,187,301 B2 * | 5/2012 | Lyons | ................ | A61B 17/0487 606/232 |
| 8,454,635 B2 * | 6/2013 | Paolitto | .............. | A61B 17/0487 24/129 R |
| 9,055,939 B2 * | 6/2015 | Fujisaki | ............. | A61B 17/0487 |
| 2003/0093091 A1 * | 5/2003 | Paolitto | .............. | A61B 17/0487 606/139 |
| 2004/0260344 A1 * | 12/2004 | Lyons | ................ | A61B 17/0487 606/232 |
| 2009/0216268 A1 * | 8/2009 | Panter | ............. | A61B 17/06166 606/222 |
| 2011/0071548 A1 * | 3/2011 | Yeh | .................... | A61B 17/0057 606/144 |
| 2012/0136389 A1 * | 5/2012 | Ashley | ............... | A61B 17/0487 606/232 |
| 2012/0165865 A1 * | 6/2012 | Fujisaki | ............. | A61B 17/0487 606/232 |
| 2013/0133240 A1 * | 5/2013 | Beitzel | ................... | A01K 83/00 43/43.16 |
| 2014/0107674 A1 * | 4/2014 | Fujisaki | ............. | A61B 17/0401 606/148 |
| 2014/0121681 A1 * | 5/2014 | Fujii | .................. | A61B 17/0401 606/144 |
| 2014/0148824 A1 * | 5/2014 | Fujisaki | ............. | A61B 17/0401 606/144 |

FOREIGN PATENT DOCUMENTS

| | | |
|---|---|---|
| JP | 2001-507972 A | 6/2001 |
| JP | 2001-508316 A | 6/2001 |
| JP | 4536698 B2 | 6/2010 |
| WO | WO 97/25927 A1 | 7/1997 |
| WO | WO 98/30151 A1 | 7/1998 |

\* cited by examiner

FIG. 1A
FIG. 1B
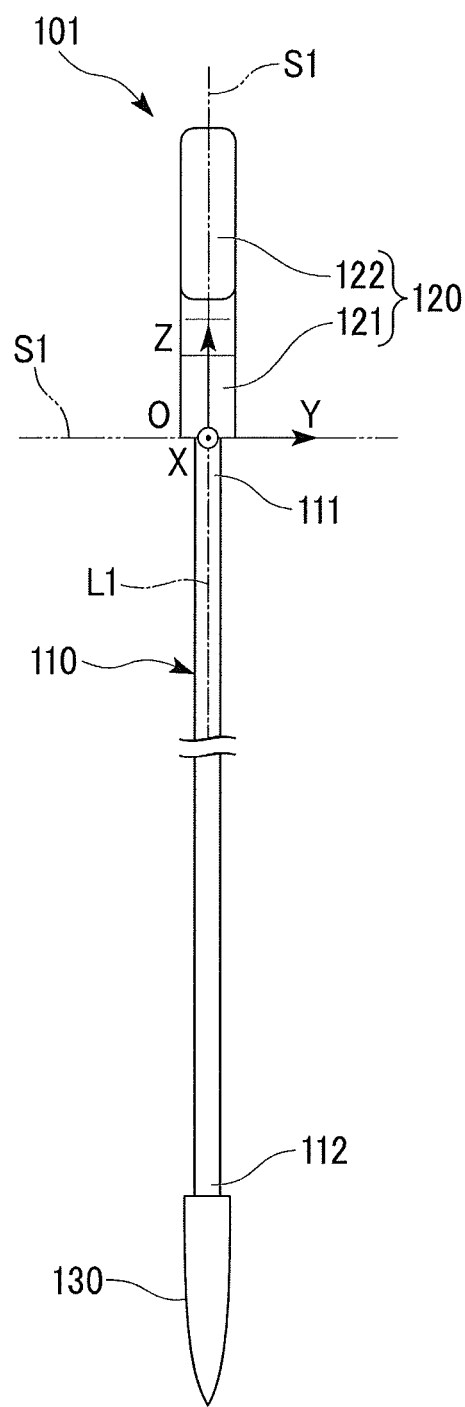
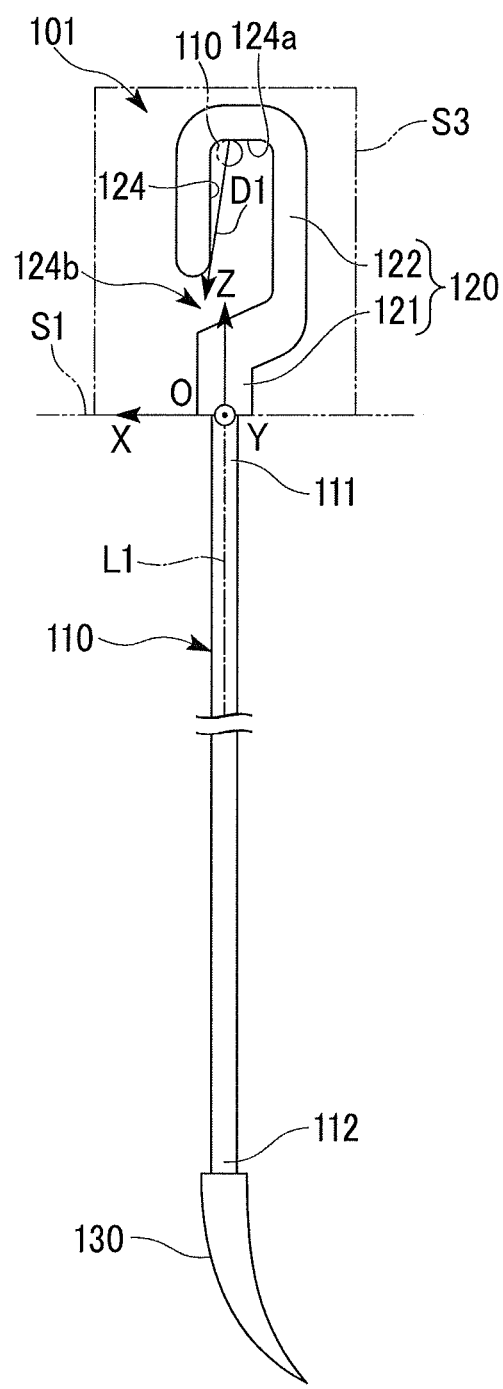

FIG. 12A
FIG. 12B
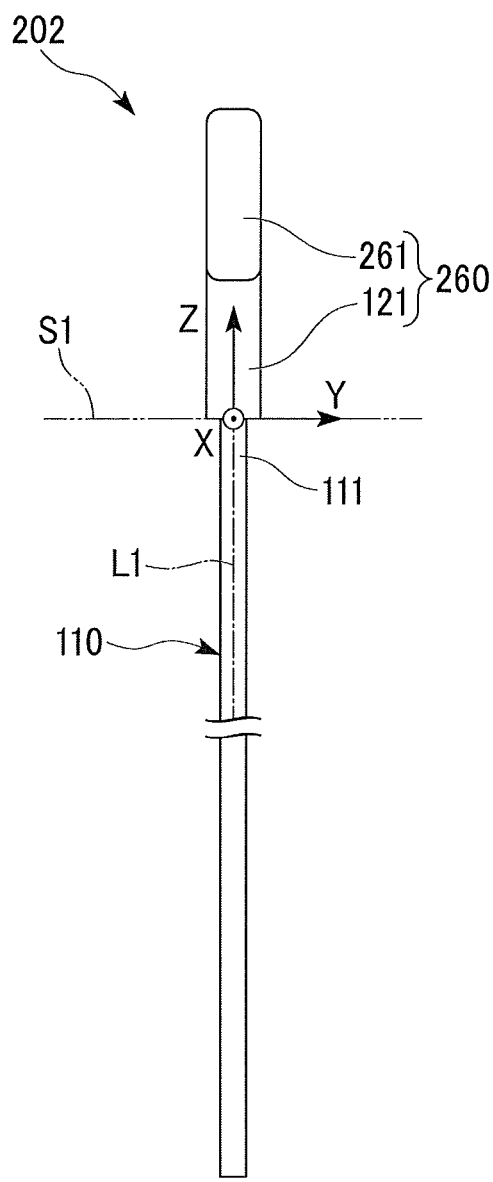
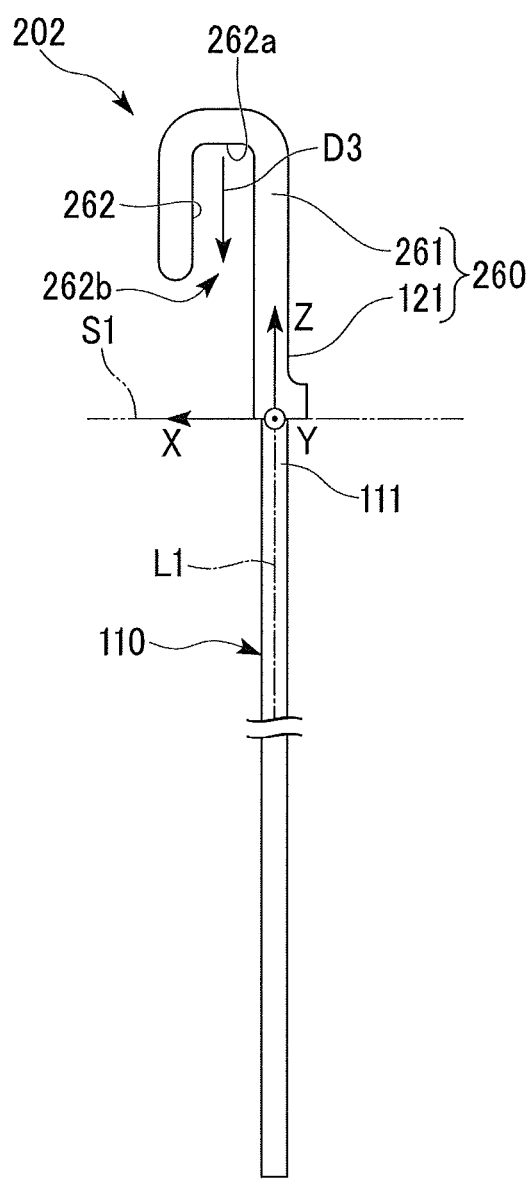

TISSUE LIGATING DEVICE

This application is a continuation application based on a PCT Patent Application No. PCT/JP2012/078553, filed on Oct. 30, 2012, whose priority is claimed on Japanese Patent Application No. 2011-239731, filed on Oct. 31, 2011, and Japanese Patent Application No. 2011-239732, filed on Oct. 31, 2011. The contents of all of the PCT Application, and the Japanese Applications are incorporated herein by reference.

BACKGROUND OF THE INVENTION

Field of the Invention

The present invention relates to a tissue ligating device provided with a suture.

Description of Related Art

In medical fields, operation of suturing or ligating tissues take a considerably important position in many manipulations, but the operation becomes difficult and requires a high level of adeptness. Recently, for the purpose of reducing stress of a patient, attempts to perform various manipulations such as surgeries using an endoscope, a laparoscope, or a thoracoscope have been made. In such an endoscopic surgery, the level of difficulty increases further in suturing or ligating because it is necessary to manipulate the suture or suture needle with long forceps, or the like.

An especially difficult part of suturing or ligating is the operation of forming a knot by tying the suture. If the knot is loosened, suturing or ligating could be undone and cause a severe disease complication. Depending on the manipulation, a plurality of knots could be formed, and in such a case the level of difficulty increases further.

A medical suturing device described in Japanese Unexamined Patent Application, First Publication No. H8-140982 is proposed. The medical suturing device includes a suturing body in which a suture is connected to a suture fastening member. The suture fastening member has a cross section formed in a U shape. The suture is formed of a bioabsorptive resin, and monofilament (single wire) and multifilament (multiple wires) are selectable for use.

To use the medical suturing device described in Japanese Unexamined Patent Application, First Publication No. H8-140982, first the suture which goes through the tissue is drawn into a U-shaped groove of the suture fastening member using a curved needle or the like. Subsequently, if the suture is pulled forcibly, and then the fastening member is deformed by caulking or ultrasonic waves, the suture drawn into the U-shaped groove is fixed to the suture fastening member. Because the knot is formed in such a way, the forming of the knot becomes easy.

SUMMARY OF THE INVENTION

According to a first aspect of the present invention, a tissue ligating device for ligating a tissue includes a suture having an elastic restoring force, and a hook-shaped member including a groove portion, connected to a first end of the suture, and disposed in a direction along a derivation direction of the suture and in a direction opposite to the derivation direction of the suture with respect to the first end of the suture.

According to a second aspect of the present invention, in the tissue ligating device according to the first aspect, at least one portion of the suture may be formed so as to be bent in a natural state.

According to a third aspect of the present invention, in the tissue ligating device according to the second aspect, the groove portion may be disposed on an opposite side of the suture with reference to the first end of the suture.

According to a fourth aspect of the present invention, in the tissue ligating device according to any one of the first aspect to the third aspect, a direction facing an opening of the groove portion from a bottom portion of the groove portion may face the first end of the suture.

According to a fifth aspect of the present invention, in the tissue ligating device according to the first aspect, the hook-shaped member may include a straight portion of which a first end portion is connected to the first end of the suture to extend in a straight-line shape, the groove portion may be formed in a second end portion opposite to the first end portion of the straight portion to which the suture is connected, and the straight portion may extend in a direction separated from the suture on a reference line, which is a central axis line of the suture through the first end of the suture.

According to a sixth aspect of the present invention, a tissue ligating device includes a suture having an elastic restoring force, and a hook-shaped member including a groove portion, connected to a first end of the suture, and disposed in a direction intersecting a derivation direction of the suture and in a direction opposite to the derivation direction of the suture with respect to the first end of the suture.

According to a seventh aspect of the present invention, in the tissue ligating device according to the sixth aspect, at least one portion of the suture may be formed so as to be bent on a bent reference plane in a natural state.

According to an eighth aspect of the present invention, in the tissue ligating device according to the seventh aspect, a direction facing an opening of the groove portion from a bottom portion of the groove portion may face a direction intersecting the bent reference plane.

According to a ninth aspect of the present invention, in the tissue ligating device according to the eighth aspect, the groove portion may be disposed at a position closer to a middle portion of the suture than a disposition reference plane which is orthogonal to the bent reference plane and includes a reference line, which is a central axis line of the suture through the first end of the suture.

According to a tenth aspect of the present invention, in the tissue ligating device according to the eighth aspect, the groove portion may be disposed at a position further separated from a middle portion of the suture than the disposition reference plane which is orthogonal to the bent reference plane and includes the reference line, which is the central axis line of the suture through the first end of the suture.

According to an eleventh aspect of the present invention, in the tissue ligating device according to the sixth aspect, the hook-shaped member may include a straight portion of which a first end portion is connected to the first end of the suture to extend in a straight-line shape, the groove portion may be formed in a second end portion opposite to the first end portion of the straight portion to which the suture is connected, and the straight portion may extend in a direction intersecting the reference line, which is the central axis line of the suture through the first end of the suture.

According to a twelfth aspect of the present invention, in the tissue ligating device according to the fifth aspect or the eleventh aspect, the direction facing the opening of the groove portion from the bottom portion of the groove portion may become substantially parallel to the straight portion, and may face the first end portion of the straight portion to which the suture is connected, and an inner wall surface of the groove portion may extend to an outer peripheral surface of the straight portion.

According to a thirteenth aspect of the present invention, the tissue ligating device according to the first aspect or the sixth aspect may further include a suture needle connected to a second end of the suture.

BRIEF DESCRIPTION OF THE DRAWINGS

FIG. 1A is a front view of a tissue ligating device according to a first embodiment of the present invention.

FIG. 1B is a side view of the tissue ligating device of the first embodiment of the present invention.

FIG. 12A is a front view of a tissue ligating device according to a second embodiment of the present invention.

FIG. 12B is a side view of the tissue ligating device according to the second embodiment of the present invention.

DETAILED DESCRIPTION OF THE INVENTION

First Embodiment

Figure 2:
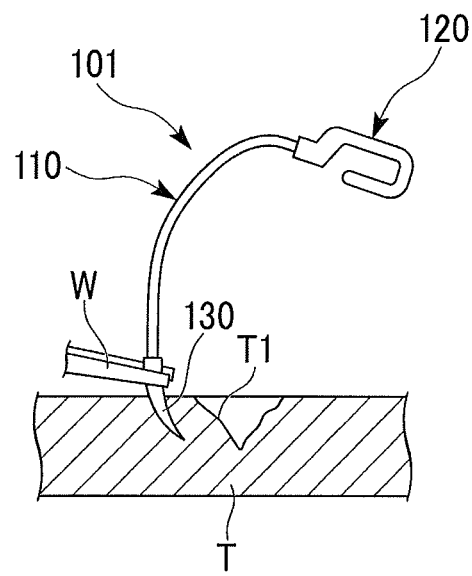
FIG. 2 is a view for describing an operation for suturing a tissue using the tissue ligating device according to the first embodiment of the present invention.

Hereinafter, a tissue ligating device (hereinafter referred to as a "device") according to a first embodiment of the present invention will be described with reference to FIGS. 1A to 11.

As illustrated in FIGS. 1A and 1B, a device 101 includes a suture 110, a hook-shaped member 120 connected to a first end 111 of the suture 110 and a suture needle 130 connected to a second end 112 of the suture 110.

In the present embodiment, the suture 110 is formed of polypropylene. The suture 110 has an elastic modulus and a cross-sectional shape adjusted so as to exert an elastic restoring force that balances gravity acting on the hook-shaped member 120 (that lifts the hook-shaped member 120). Meanwhile, the elastic restoring force referred to here means a force whereby the suture will return to its original shape when a suture of any shape is deformed. In other words, it is the force generated in an elastically deformed suture.

It is preferable that the elastic restoring force of the suture 110 be great within a range not impeding the operator's manipulation. The suture 110 is configured such that the elastically deformable distortion range becomes relatively large.

As the material forming the suture 110, a resin or a metal may be suitably used in addition to polypropylene as long as the suture 110 is configured such that the elastic restoring force as mentioned above can be exerted.

Resins that can be used in the suture 110 are classified into absorbent resins and nonabsorbent resins. The absorbent resins include PGA, PLA, PDS, TMC, poly-epsilon-caprolactone and a copolymer thereof. The nonabsorbent resins include nylon, polyester, polypropylene, polybutester, fluorine resin and PET or the like.

On the other hand, as an example of the metal that can be used in the suture 110, stainless steel, a Co—Cr alloy, β titanium, nickel titanium, pure Ti, a Ti alloy, a Mg alloy or the like can be included.

Meanwhile, it is preferable that the mass of the hook-shaped member 120 be about 5 g or less for the skin suturing, for example, and about 0.01 g or less for a fine area such as in cardiovascular surgery.

The hook-shaped member 120 includes a straight portion 121 of which a first end portion is connected to the first end 111 of the suture 110 and extends in a straight-line shape, and a bent portion 122 formed at a second end portion 122 opposite to the first end portion of the straight portion 121 to which the suture 110 is connected.

Meanwhile, if the hook-shaped member 120 and the suture 110 are the same in material, they may be integrally configured.

Here, for the convenience of description, taking the first end 111 of the suture 110 as an origin O, the central axis line on the origin O of the suture 110 is defined as a reference line L1.

A Z axis is defined on the reference line L1, and the direction separating from the suture 110 is taken as a positive direction of the Z axis.

By defining the reference plane S1 that passes the origin O and is orthogonal to the reference line L1, a rectangular coordinate system of the right hand system is defined with the X axis and Y axis arranged on the reference plane S1 and the above-mentioned Z axis.

In the rectangular coordinate system XYZ defined as this, the straight portion 121 extends in the positive direction of the Z axis on the reference line L1, namely, the Z axis. In this case, the derivation direction in which the suture 110 is derived is defined as a negative direction of the Z axis.

A fixing hole not shown is formed in the end portion of the straight portion 121. The straight portion 121 is connected to the suture 110 by pressing the first end 111 of the suture 110 into the fixing hole and fixing the first end 111 and the straight portion 121 with an adhesive agent or by welding.

The bent portion 122 extends in the negative direction of the X axis from the end portion of the straight portion 121, extends in the positive direction of the Z axis at the distal end thereof, extends in the positive direction of the X axis at the distal end thereof, and extends in the negative direction of the Z axis at the distal end thereof. The bent portion 122 is formed in a shape in which one part of the side of the rectangle is cut away as a whole.

A groove portion 124 in which the suture 110 can be engaged is formed in the bent portion 122. The bent portion 122 is bent on a reference plane S3, which is a ZX plane, so that the groove portion 124 penetrates the bent portion 122 in the direction of the Y axis. The direction D1 facing from the bottom portion 124a of the groove portion 124 to the opening 124b of the groove portion 124 is set in such a way that it becomes a direction facing from the side on which the Z axis is positive to the side on which the Z axis is negative. The depth of the groove portion 124 (the distance from the bottom portion 124a to the opening 124b of the groove portion 124) is set to be greater than the outer diameter of the suture 110. The groove portion 124 is disposed on the side on which the Z axis is positive (further in the positive direction of the Z axis than the reference plane S1).

In the present embodiment, the straight portion 121 and the bent portion 122 are formed integrally by bending-processing a wire formed of stainless steel. The hook-shaped member 120 is formed more solidly than the suture 110, so it can be plastically deformed by caulking.

The cross-sectional shape of the hook-shaped member 120 defined by a plane orthogonal to the direction in which the hook-shaped member 120 extends is formed in a rectangular shape.

The size of the hook-shaped member 120 is preferably about 10 mm or less in the case of skin suturing, for example, and preferably about 2 mm or less in a finer area such as cardiovascular surgery. The hook-shaped member 120 is formed to be considerably small.

Various well-known needles may be used as the suture needle 130, such as a straight-line shaped needle, a bent needle, a needle of which only a distal end portion is bent and the other portion is formed in a straight-line shape may be chosen suitably considering the suturing portion. There are no particular limitations to the connection aspect of the suture 110 and the suture needle 130. Specifically, the method includes adhesion, fusion, or passing the end portion of the suture 110 through the hole formed in the end portion of the suture needle 130 and tying the suture 110.

Next, the operation using the device 101 configured as above will be described by taking the case of suturing a lacerated wound portion formed on the surface of a tissue as an example.

First, the operator grasps the suture needle 130 of the device 101 with a grasping forceps W, for example, as shown in FIG. 2, and punctures a portion near a lacerated wound portion T1 of the tissue T with the suture needle 130.

Figure 3:
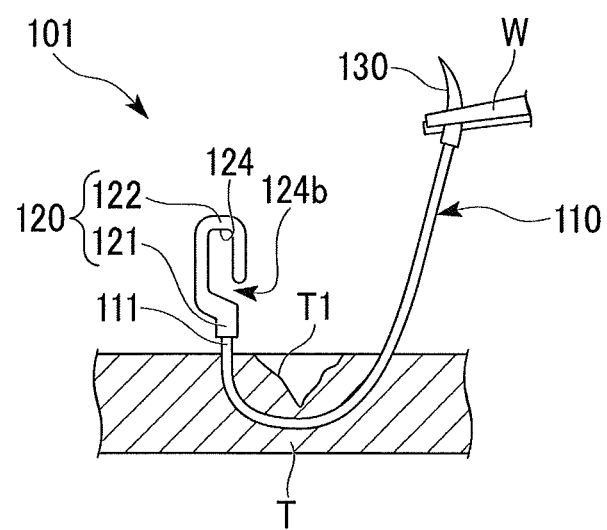
FIG. 3 is a view for describing the operation for suturing the tissue using the tissue ligating device according to the first embodiment of the present invention.

As shown in FIG. 3, the operator passes the suture needle 130 and the suture 110 into the tissue T so as to encircle the lacerated wound portion T1. By pulling the suture needle 130 so as to be separated from the lacerated wound portion T1, the first end 111 of the suture 110 is made to protrude from the tissue T as much as the height suitable for the hook-shaped member 120 to be hooked on the suture 110. The height for protruding the first end 111 is preferably about several mm to about several cm, for example.

At this time, because the suture 110 can exert the above-mentioned elastic restoring force, the hook-shaped member 120 that is supported by the first end 111 of the suture 110 is kept separated from the tissue T without falling over the tissue T as the hook-shaped member 120 is affected by gravity.

Figure 4:
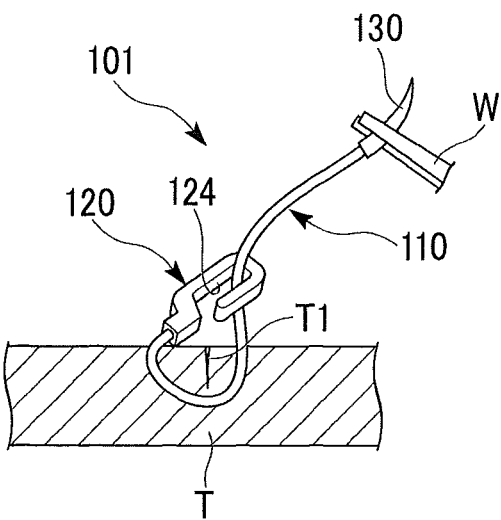
FIG. 4 is a view for describing the operation for suturing the tissue using the tissue ligating device according to the first embodiment of the present invention.

The grasping forceps W that grasps the suture needle 130 is moved toward the hook-shaped member 120, the suture 110 is engaged in the groove portion 124 through the opening 124b, and a loop is formed with the suture 110. As shown in FIG. 4, while maintaining the state in which the suture 110 is engaged in the hook-shaped member 120, the suture needle 130 is pulled so as to be separated from the lacerated wound portion T1. Accordingly, the hook-shaped member 120 abuts the tissue T and the suture 110 moves into the groove portion 124, so that the tissue T around the lacerated wound portion T1 is bandaged by the suture 110 and the opening of the lacerated wound portion T1 is closed.

Figure 5:
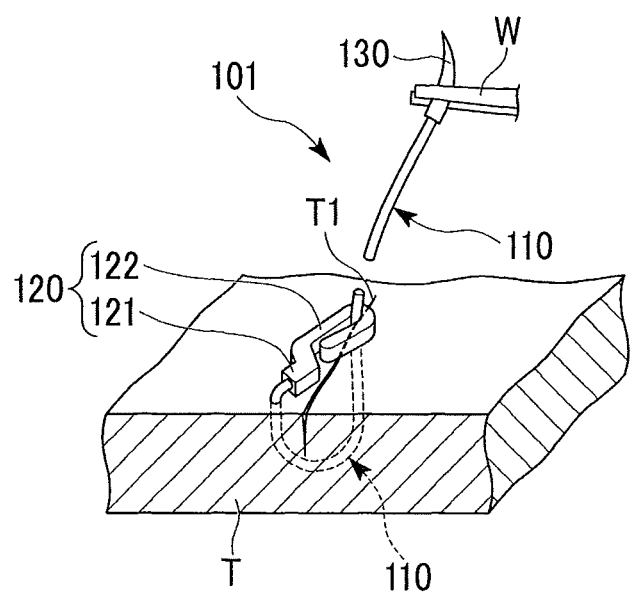
FIG. 5 is a view for describing the operation for suturing the tissue using the tissue ligating device according to the first embodiment of the present invention.

With the suture needle 130 pulled so as to be separated from the lacerated wound portion T1, the bent portion 122 of the hook-shaped member 120 is caulked with another grasping forceps not shown so as to collapse from outside, and the hook-shaped member 120 is fixed to the suture 110, as shown in FIG. 5. Thus, the tissue T is ligated by forming a knot with the suture 110 and the caulked hook-shaped member 120.

The suture 110 is cut on the nearer side of the suture needle 130 than the caulked hook-shaped member 120 with a medical knife. The suture needle 130 and the cut suture 110 are then removed to end the manipulation.

As described above, in the device 101 according to the present embodiment, the bent portion 122 is kept separated from the tissue T by the first end 111 of the loop formed with the suture 110 due to the elastic restoring force of the suture 110 and the deposition of the straight portion 121 and the bent portion 122 as described above, even if the suture 110 is passed through the tissue T from the second end 112.

By engaging the suture 110 that has passed through the tissue T in the groove portion 124 of the bent portion 122 that is floated from the tissue T, the suture 110 can be easily engaged in the hook-shaped member 120.

Since the device 101 is provided with the suture needle 130, it is possible to make the suture 110 connected to the suture needle 130 pass through the tissue T easily.

In general, the operator performs manipulation while observing from the side separated from the tissue T. Accordingly, the hook-shaped member 120 that is separated from the tissue T becomes positioned on the operator's side, so it becomes easy for the operator to observe the hook-shaped member 120. Therefore, it is possible to caulk the hook-shaped member 120 easily with the grasping forceps W or the like.

The device 1 according to the present embodiment can be modified variously as will be described below.

Figure 6:
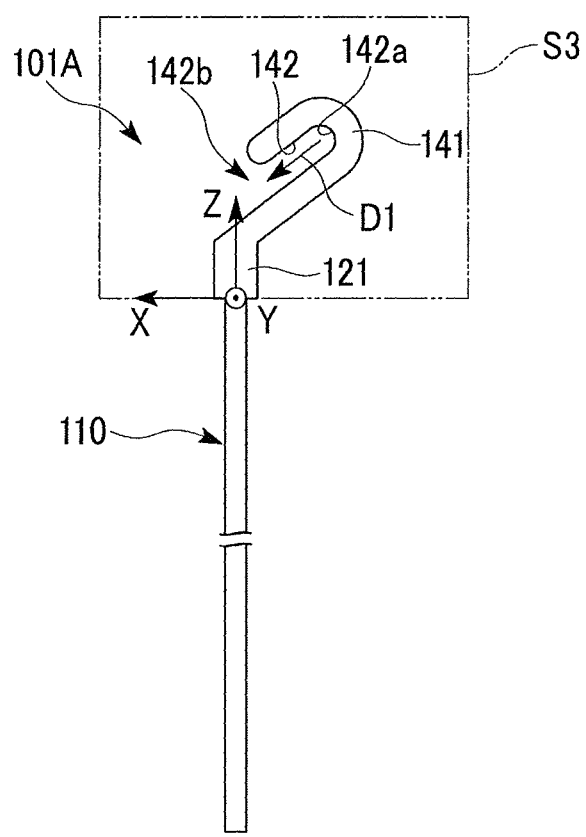
FIG. 6 is a side view of a tissue ligating device according to a modified example of the first embodiment of the present invention.

For example, as a device 101A illustrated in FIG. 6, a bent portion 141 in which a groove portion 142 is formed may be provided, instead of the bent portion 122 and the suture needle 130 of the device 101 of the first embodiment.

The bent portion 141 is formed in a substantial U shape and is disposed on a reference plane S3, which is a ZX plane. The direction D2 facing the opening 142b from the bottom portion 142a of the groove portion 142 is set in a direction between the positive direction of the X axis and the negative direction of the Z axis. In the bent portion 141 formed in a substantial U shape, an end portion on a side of the negative direction of the Z axis is connected to the straight portion 121. The opening 142b of the groove portion 142 is disposed further in the positive direction of the Z axis than the connection portion of the straight portion 121 and the bent portion 141. The straight portion 121 and the bent portion 141 are integrally formed of the same material as the hook-shaped member 120 described above.

Figure 7:
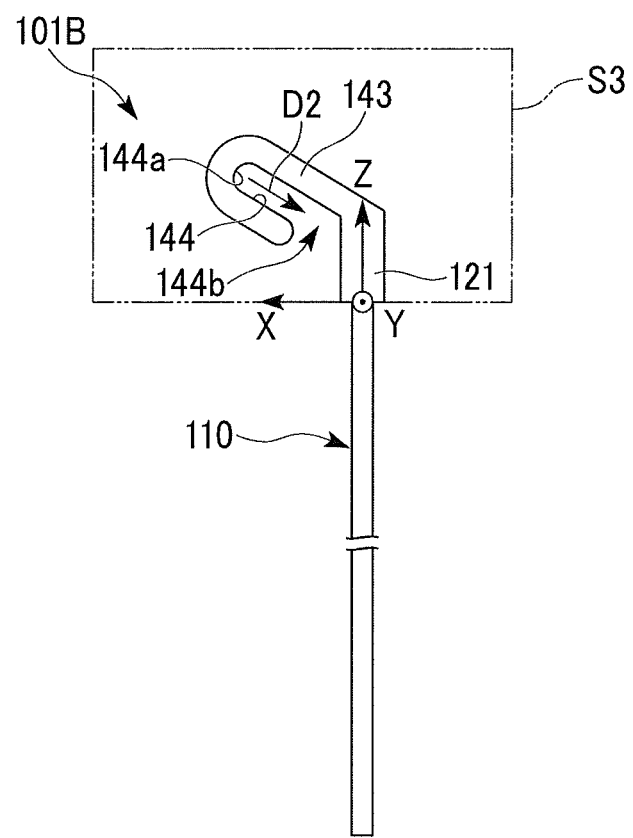
FIG. 7 is a side view of the tissue ligating device according to the modified example of the first embodiment of the present invention.

A device 101B illustrated in FIG. 7 includes a bent portion 143 in which a groove portion 144 is formed, instead of the bent portion 122 and the suture needle 130 of the device 101 of the first embodiment.

The bent portion 143 is formed in a substantial U shape and is disposed on the reference plane S3. The direction D2 facing the opening 144b from the bottom portion 144a of the groove portion 144 is set in a direction between the negative direction of the X axis and the negative direction of the Z axis. In the bent portion 143 formed in a substantial U shape, the end portion on a side of the negative direction of the X axis is connected to the straight portion 121, and the opening 144b of the groove portion 144 is disposed on a nearer side of the positive direction of the X axis than the connection portion of the straight portion 121 and the bent portion 143.

Figure 8:
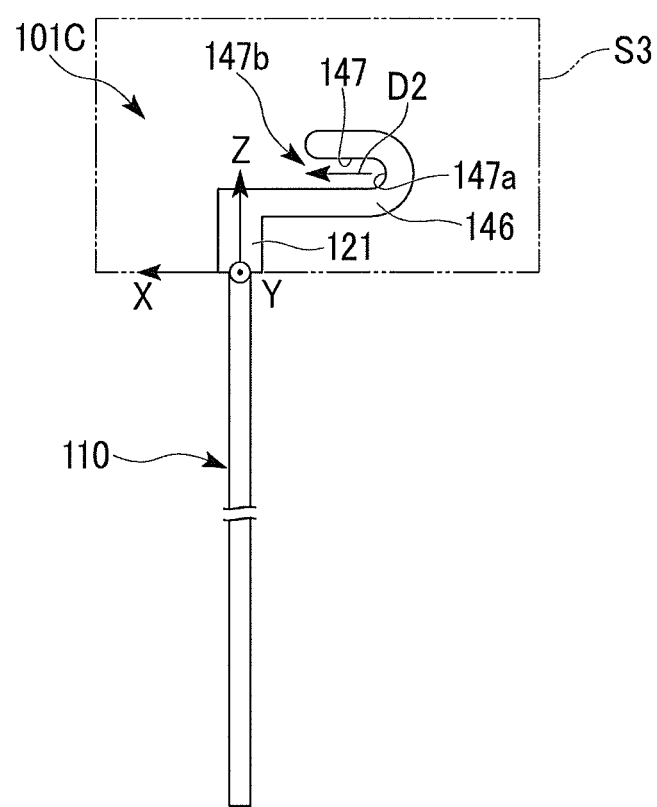
FIG. 8 is a side view of the tissue ligating device according to the modified example of the first embodiment of the present invention.

A device 101C illustrated in FIG. 8 includes a bent portion 146 in which a groove portion 147 is formed, instead of the bent portion 141 of the device 101A of the above modified example.

The bent portion 146 is formed in a substantial U shape and is disposed on the reference plane S3. The direction D2 facing the opening 147b from the bottom portion 147a of the groove portion 147 is set in the positive direction of the X axis. In the bent portion 146 formed in a substantial U shape, the part which is the end portion on a side of the positive direction of the X axis and becomes the end portion on a side of the negative direction of the Z axis is connected to the straight portion 121. The opening 147b of the groove portion 147 is disposed on a nearer side of the positive direction of the Z axis than the connection portion of the straight portion 121 and the bent portion 146.

Figure 9:
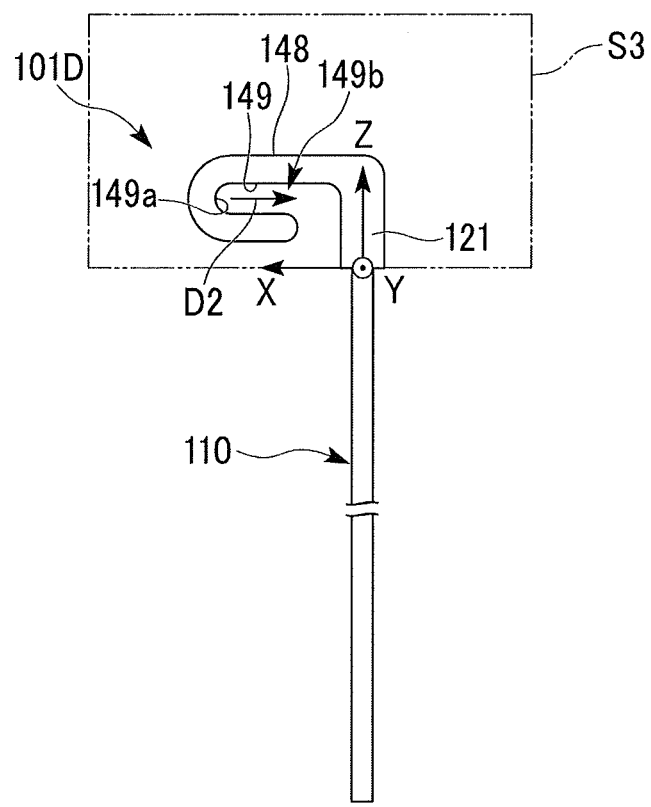
FIG. 9 is a side view of the tissue ligating device according to the modified example of the first embodiment of the present invention.

A device 101D illustrated in FIG. 9 includes a bent portion 148 in which a groove portion 149 is formed, instead of the bent portion 143 of the device 101B of the above modified example.

The bent portion 148 is formed in a substantial U shape and is disposed on the reference plane S3. The direction D2 facing the opening 149b from the bottom portion 149a of the groove portion 149 is set in the negative direction of the X axis. In the bent portion 148 formed in a substantial U shape, the part which is the end portion on a side of the negative direction of the X axis and becomes the end portion on a side of the positive direction of the Z axis is connected to the straight portion 121. The opening 149b of the groove portion 149 is disposed on a nearer side of the negative direction of the Z axis than the connection portion of the straight portion 121 and the bent portion 148.

Figure 10:
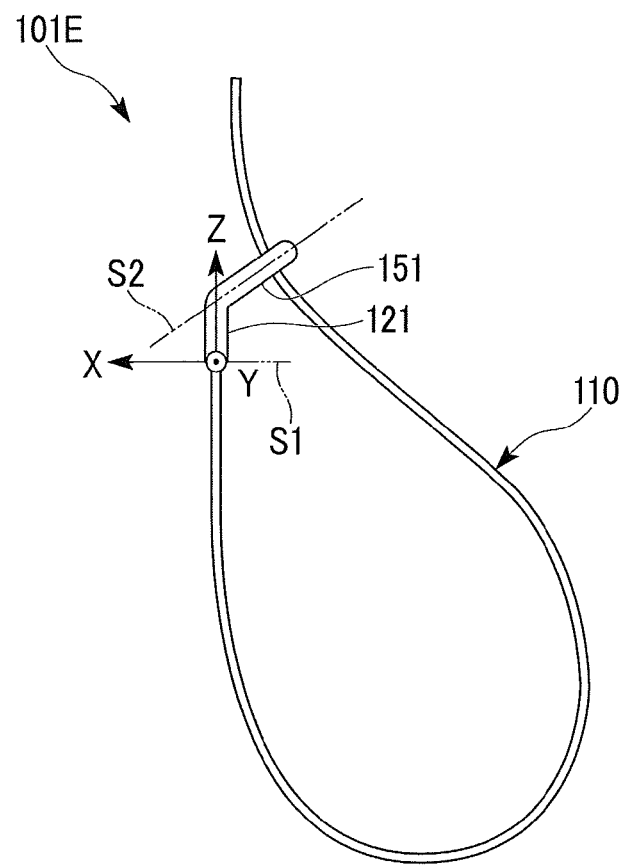
FIG. 10 is a side view of the tissue ligating device according to the modified example of the first embodiment of the present invention.
Figure 11:
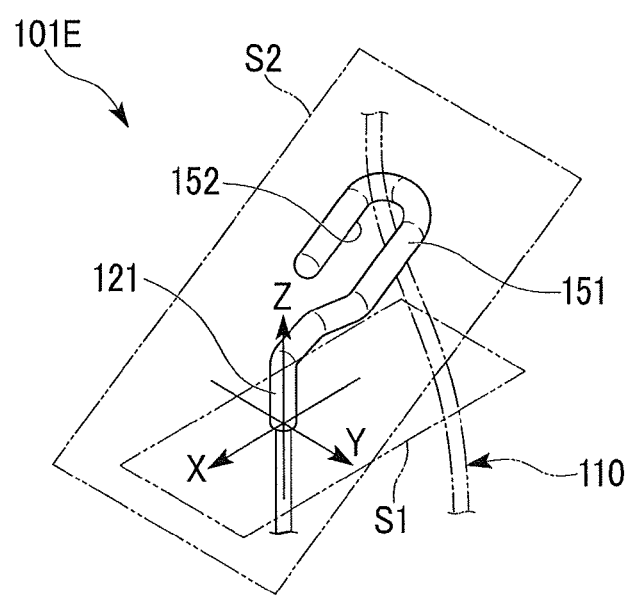
FIG. 11 is a perspective view of major parts of the tissue ligating device according to the modified example of the first embodiment of the present invention.

A device 101E illustrated in FIGS. 10 and 11 includes a bent portion 151 in which a groove portion 152 is formed, instead of the bent portion 122 and the suture needle 130 of the device 101 of the first embodiment.

The modified example shows a state in which the suture 110 is engaged in the groove portion 152.

The bent portion 151 is formed in a same way as the above-mentioned bent portion 122, but is disposed on a different plane compared with the bent portion 122. That is, whereas the bent portion 122 is disposed on the reference plane S3, which is a ZX plane, the bent portion 151 is disposed on a second reference plane S2. The second reference plane S2 is a plane which passes through the end portion opposite to the part where the suture 110 is connected in the straight portion 121 and intersects without being orthogonal to the Z axis. The bent portion 151 is disposed on the second reference plane S2 so as to be separated from the straight portion 121.

In the present modified example, the groove portion 152 intersects with respect to the suture 110, but the straight portion 121 is disposed in a direction along the derivation direction of the suture 110 and in the direction opposite to the derivation direction of the suture 110. Accordingly, as a whole of the hook-shaped member having the groove portion 152, it is disposed in the direction along the derivation direction of the suture 110 and in the direction opposite to the derivation direction of the suture 110.

Thus, it is possible to engage the suture 110 in the hook-shaped member easily because the bent portion is kept separated from the tissue T by the elastic restoring force of the suture 110 in the devices 101A, 101B, 101C, 101D and 101E configured as above, like in the device 1 according to the present embodiment.

Second Embodiment

Next, a second embodiment of the present invention will be described with reference to FIGS. 12A, 12B and 13. The same parts as in the above-mentioned embodiment will be denoted by the same reference numerals, a description thereof will be omitted, and only differences will be described.

As illustrated in FIGS. 12A and 12B, a device 202 according to the present embodiment includes a hook-shaped member 260 instead of the hook-shaped member 120 and the suture needle 130 of the device 101 of the first embodiment.

The hook-shaped member 260 includes the above-mentioned straight portion 121 and a bent portion 261 in which a groove portion 262 is formed.

The groove portion 262 is formed such that the direction D3 facing the opening 262b of the groove portion 262 from the bottom portion 262a of the groove portion 262 faces the first end 111 of the suture 110. In other words, the groove portion 262 is formed such that the direction D3 becomes substantially parallel to the reference line L1 (the straight portion 121) and also faces the first end portion of the straight portion 121 to which the suture 110 is connected.

The inner wall surface of the groove portion 262 continues into (directly connected to) the outer peripheral surface of the straight portion 121.

Next, the operation using the device 202 configured as above will be described by taking the case of suturing a blood vessel as an example.

Figure 13:
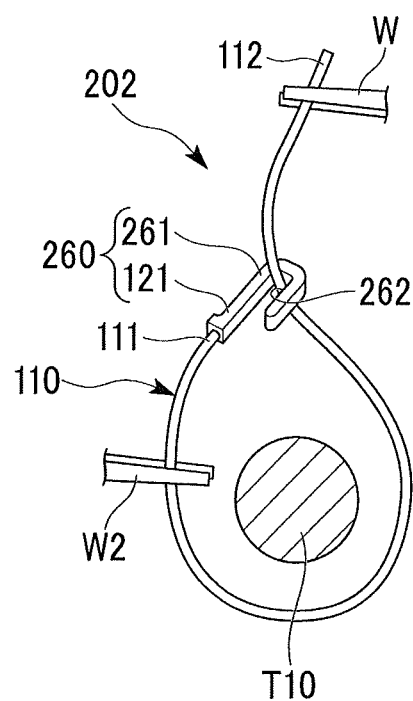
FIG. 13 is a view for describing an operation for suturing a blood vessel using the tissue ligating device according to the second embodiment of the present invention.

First, the operator grasps the second end 112 of the suture 110 with a grasping forceps W and the first end 111 thereof with another grasping forceps W2 (see FIG. 13).

By the grasping forceps W2, the position of the first end 111 of the suture 110 is maintained close to the blood vessel (the tissue) T10. Because the suture 110 can exert the above-mentioned elastic restoring force, the hook-shaped member 260 is kept separated from the blood vessel T10.

As illustrated in FIG. 13, by the grasping forceps W, the second end 112 of the suture 110 is routed around the blood vessel T10 against the elastic restoring force of the suture 110 to form a loop, and the middle portion of the suture 110 abuts the first end portion of the straight portion 121 to which the suture 110 is connected. If the force maintaining the position of the second end 112 of the suture 110 by the grasping forceps W is weakened, the suture 110 is deformed by its own elastic restoring force so as to widen the formed loop. Accordingly, the middle portion of the suture 110 is moved along the straight portion 121 so as to be separated from the first end 111 of the suture 110, and the suture 110 is engaged in the groove portion 262.

The grasping is released from the grasping forceps W2, and while the suture 110 is engaged in the hook-shaped member 260, the grasping forceps W is pulled to separate it from the blood vessel T10. Accordingly, the blood vessel T10 is bandaged by the suture 110. The bent portion 261 of the hook-shaped member 260 is caulked with the grasping forceps W2 so as to collapse from outside and the hook-shaped member 260 is fixed to the suture 110. The suture 110 is cut nearer the second end 112 than the fixed hook-shaped member 260 to end the manipulation.

As described above, in the device 202 according to the present embodiment, because the direction D3 facing the opening 262b from the bottom portion 262a of the groove portion 262 is formed so as to face the first end 111 of the suture 110, it is possible to engage the suture 110 in the groove portion 262 easily by moving the middle portion of the suture 110 toward the groove portion 262 after moving the middle portion of the suture 110 toward the first end 111 of the suture 110.

Further, by moving the middle portion of the suture 110 that abuts the straight portion 121 so as to slide toward the bent portion 261 along the straight portion 121, it is possible to engage the suture 110 in the groove portion 262 more easily.

If the force maintaining the position of the second end 112 of the suture 110 by the grasping forceps W is weakened, the suture 110 can be automatically engaged in the groove portion 262 by the elastic restoring force of the suture 110.

In addition, because the opening 262b of the groove portion 262 is formed so as to face the first end portion of the straight portion 121 to which the suture 110 is connected, the operator can easily recognize the direction D3 of the opening 262b.

Figure 14:
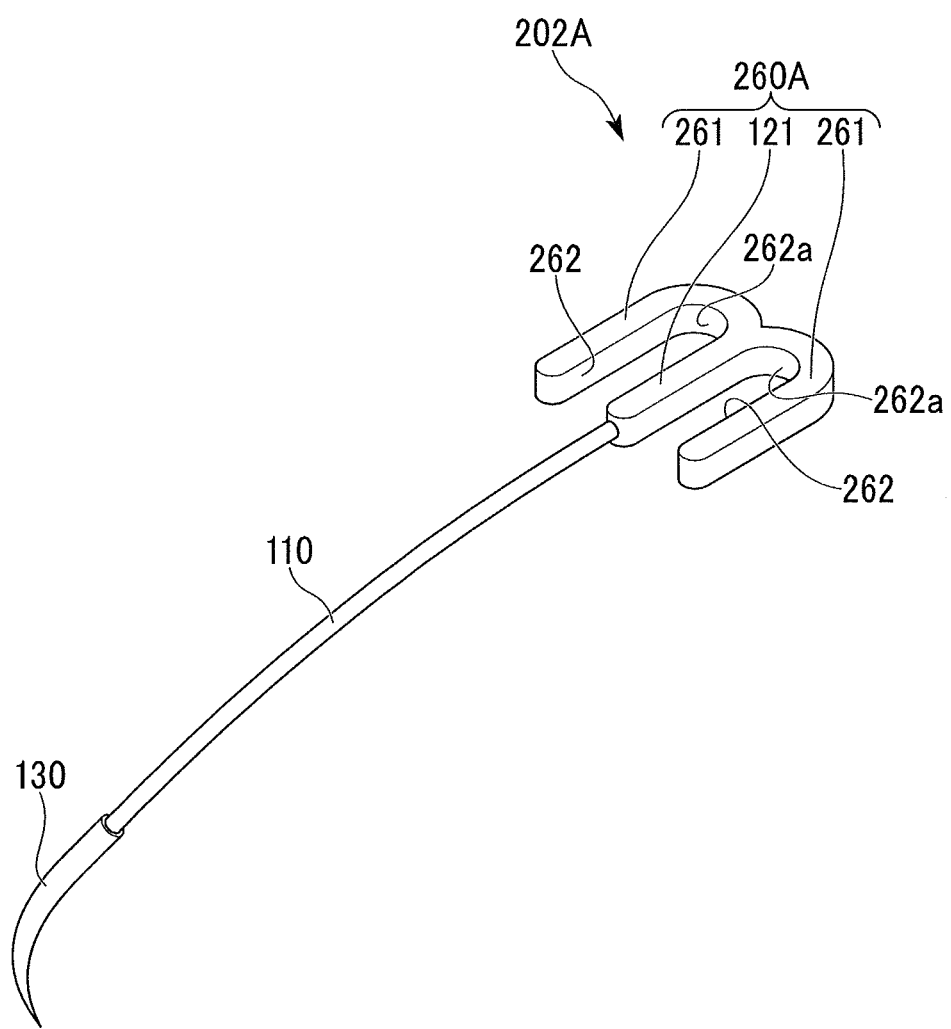
FIG. 14 is a perspective view of a tissue ligating device according to a modified example of the second embodiment of the present invention.

Meanwhile, as illustrated in FIG. 14, the device 202 according to the present embodiment may be a device 202A which includes a hook-shaped member 261 having a two bent portions 261 and two groove portions 262. That is, the device 202A illustrated in FIG. 14 includes a shape having two hook shaped portions configured by the bent portion 261. According to the device 202A, since having two hook shaped portions configured by the bent portions 261, it is possible to include two groove portions 262 and to engage the suture 110 easily.

Third Embodiment

Next, a third embodiment of the present invention will be described with reference to FIGS. 15 to 19. The same parts as in the above-mentioned embodiments will be denoted by the same reference numerals, a description thereof will be omitted here, and only differences will be described.

Figure 15:
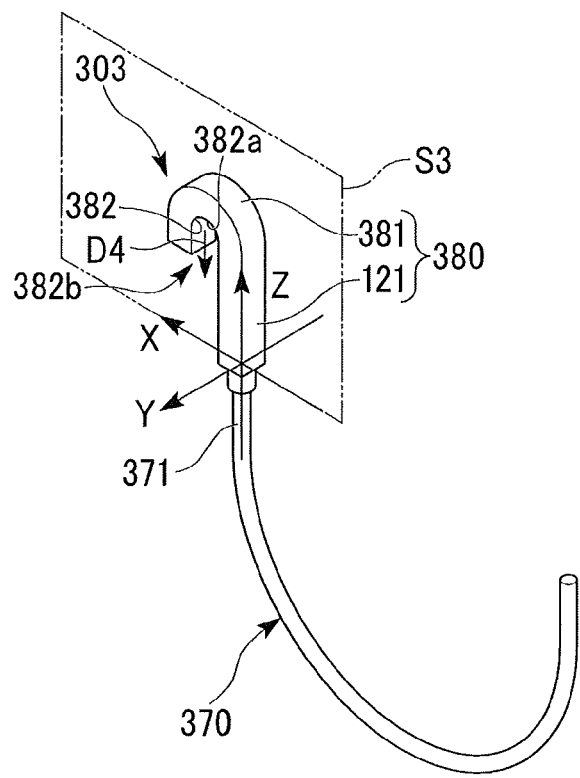
FIG. 15 is a perspective view of a tissue ligating device according to a third embodiment of the present invention.
Figure 16:
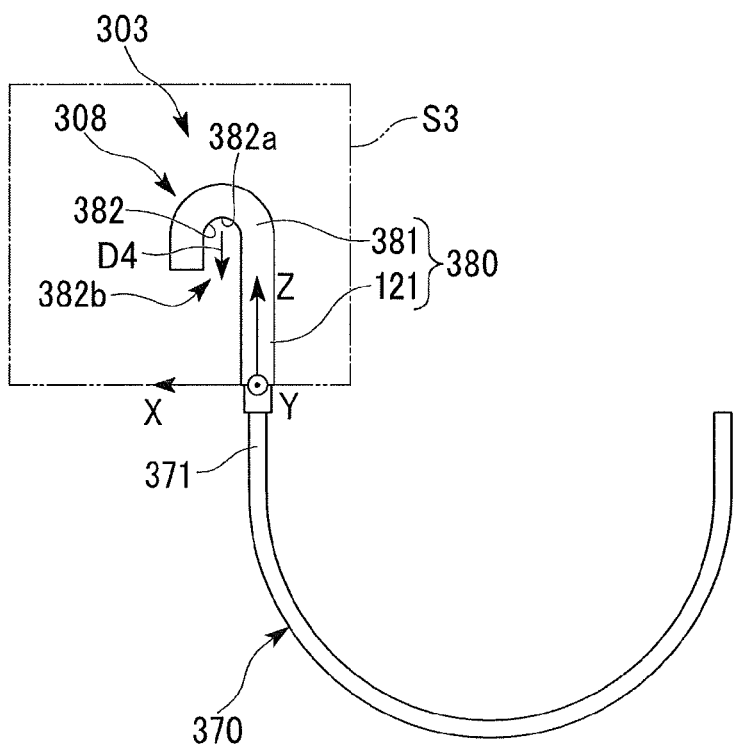
FIG. 16 is a side view of the tissue ligating device according to the third embodiment of the present invention.

As shown in FIGS. 15 and 16, a device 303 according to the present embodiment includes a suture 370 and a hook-shaped member 380 connected to a first end 371 of the suture 370.

The suture 370 is formed in a circular arc shape which is bent on a reference plane S3 in a natural state over the entire length thereof. In the present embodiment, the suture 370 is bent about 180 degrees at a central angle. The suture 370 is formed of polypropylene which has high spring properties (high elastic restoring force). The shape of the suture 370 that is bent in a natural state can be formed by heat treating propylene, for example. A material forming the suture 370 includes a resin or a metal. The resin can be classified as an absorbent resin or a nonabsorbent resin. The absorbent resin includes PGA, PLA, PDS, TMC, poly-epsilon-caprolactone or a copolymer thereof. The nonabsorbent resin includes nylon, polyester, polypropylene, polybutester, fluorine resin, PET or the like. As an example of the metal, stainless steel, a Co—Cr alloy, β titanium, nickel titanium, pure Ti, a Ti alloy, a Mg alloy or the like can be included.

The hook-shaped member 380 includes the above-mentioned straight portion 121 and a bent portion 381 formed at the second end portion opposite to the first end portion of the straight portion 121 to which the suture 370 is connected.

The bent portion 381 is formed in a circular arc shape having a central angle of about 180 degrees. The bent portion 381 is disposed on the reference plane S3 and is disposed on the opposite side of the suture 370 with respect to the X axis and the Z axis, respectively. The direction D4 facing the opening 382b of the groove portion 382 from the bottom portion 382a of the groove portion 382 in which the bent portion 381 forms is set so as to become the negative direction of the Z axis.

The groove portion 382 of the hook-shaped member 380 is disposed on the opposite side of the suture 370 with reference to the first end 371 of the suture 370. That is, on the reference plane S3, the suture 370 is disposed on the negative side of the X axis and the groove portion 382 is disposed on the positive side of the X axis.

The hook-shaped member 380 is formed of the same material as the hook-shaped member 120.

Next, the operation using the device 303 configured as above will be described by taking the case of suturing a blood vessel T10 as an example.

Figure 17:
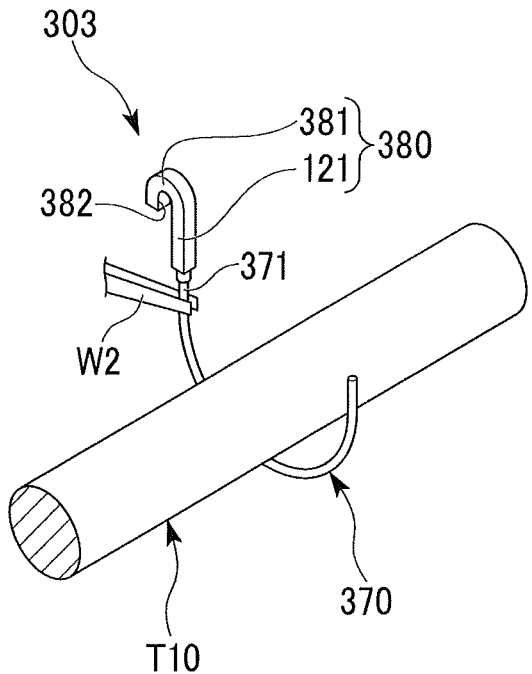
FIG. 17 is a view for describing an operation for suturing a blood vessel using the tissue ligating device according to the third embodiment of the present invention.

First, the operator grasps the first end 371 of the suture 370 with the grasping forceps W2 and disposes the suture 370 so as to encircle the blood vessel T10, as illustrated in FIG. 17. Because the suture 370 is configured so as to be bent in a natural state, the suture 370 can be easily disposed so as to encircle the blood vessel T10. Further, because the device 303 is configured as described above, the bent portion 381 is disposed so as to face the opposite side of the blood vessel T10.

Figure 18:
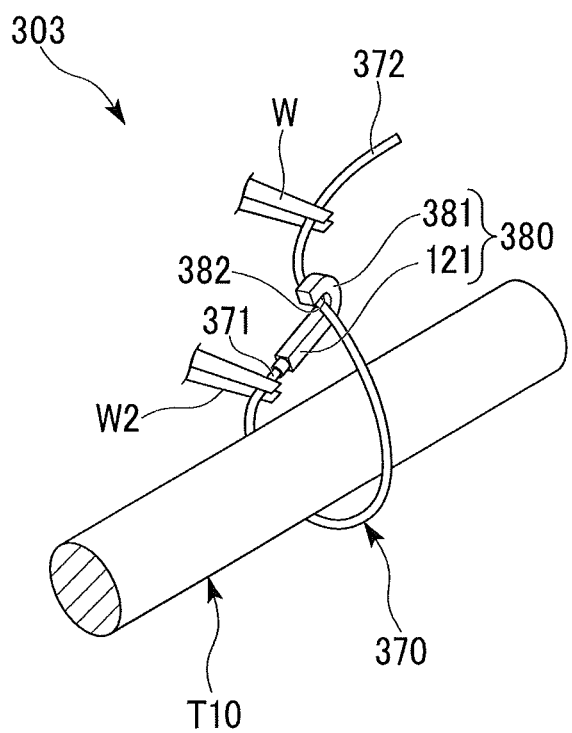
FIG. 18 is a view for describing the operation for suturing the blood vessel using the tissue ligating device according to the third embodiment of the present invention.

Next, as illustrated in FIG. 18, with the position at the first end 371 of the suture 370 being maintained by the grasping forceps W2, the second end 372 of the suture 370 is grasped with the grasping forceps W. When the middle portion of the suture 370 abuts the first end portion of the straight portion 121 to which the suture 370 is connected and the middle portion of the suture 370 is moved so as to be separated from the first end 371 of the suture 370 along the straight portion 121, the suture 370 is engaged in the groove portion 382.

At this time, by using the force whereby the suture 370 widens the loop, it is possible to move the suture 370 along the straight portion 121.

The description of the sequence after this will be omitted since it is the same as that of the device 202 in the second embodiment.

Figure 19:
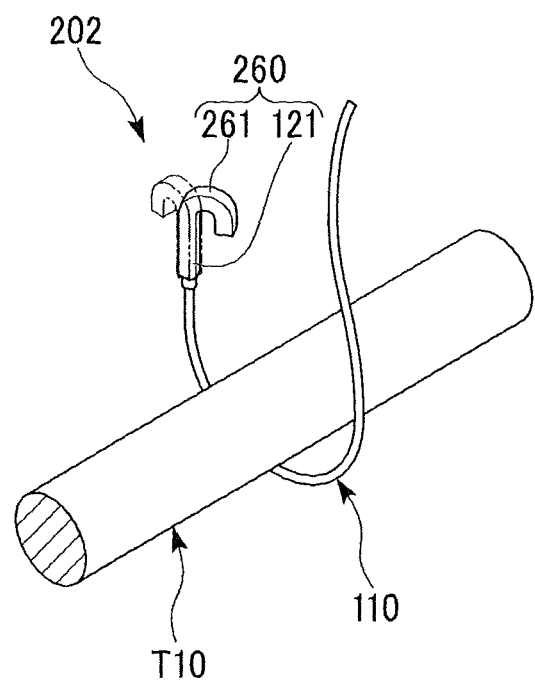
FIG. 19 is a view for describing an operation for suturing a blood vessel in the case of using a tissue ligating device in which a suture is not formed so as to be bent in a state of nature.

In the above-mentioned device 202, because the suture 110 is not formed so as to be bent in the natural state, the direction of the bent portion 261 with respect to the suture 110 is not determined when the blood vessel T10 is encircled with the suture 110, as illustrated in FIG. 19.

In the device 303 according to the present embodiment, the suture 370 is formed so as to be bent in a natural state. Therefore, when the suture 370 is disposed so as to encircle the blood vessel T10, the direction of the hook-shaped member 380 with respect to the suture 370 is determined. Accordingly, it is possible to engage the suture 370 in the groove portion 382 easily even when it is difficult for the operator to confirm a position of the groove portion 382 visually because the hook-shaped member 380 is formed considerably small.

Further, the groove portion 382 is disposed on the opposite side of the suture 370 with reference to the first end 371 of the suture 370. Accordingly, a problem in which it becomes difficult to engage the suture 370 in the groove portion 382 as the blood vessel T10 becomes an obstacle because the groove portion 382 and the blood vessel T10 are disposed on the same side with respect to the straight portion 121 does not occur. Therefore, it is possible to engage the suture 370 in the groove portion 382 easily using the elastic restoring force of the suture 370.

In the present embodiment, the suture 370 is formed so as to be bent in a natural state over the entire length thereof. However, at least one portion of the suture in the longitudinal direction may be formed so as to be bent in a natural state. Even in this case, it is possible to bring about the same effect as the present embodiment.

Further, the disposition of the central angle of the bent portion 381 in a natural state or the groove portion 382 is not limited to that described above, but may be deposited in any way as long as it is easy to manipulate according to the shape or position of the tissue to be ligated.

While the first to third embodiments of the present invention have been described in detail with reference to the drawings, a specific configuration is not limited to these embodiments but includes modifications of the configuration within the scope not departing from the spirit of the present invention. Further, configurations shown in the respective embodiments may be combined suitably.

For example, in the first to third embodiments, it is assumed that a rectangular shape is taken as the cross-sectional shape of the hook-shaped member defined by the plane orthogonal to the direction in which the hook-shaped member extends. However, the cross-sectional shape is not limited to a rectangular shape, but may be a circular or elliptical shape or a shape of a polygon other than a rectangle.

In the first to third embodiments, it is assumed that the hook-shaped member is formed by bending-processing a wire, but it may be configured by forming the groove portion or the like in a block formed of stainless steel by laser processing, wire-cut processing, or machine processing.

Further, it is assumed that the hook-shaped member includes a straight portion extending in a straight-line shape, but it may include a wavy shape or spherical shape instead of the straight-line shape.

Further, the hook-shaped member may be configured in such a way that the bent portion of the hook-shaped member is connected to first end of the suture 110 without having a straight portion.

Figure 20A:
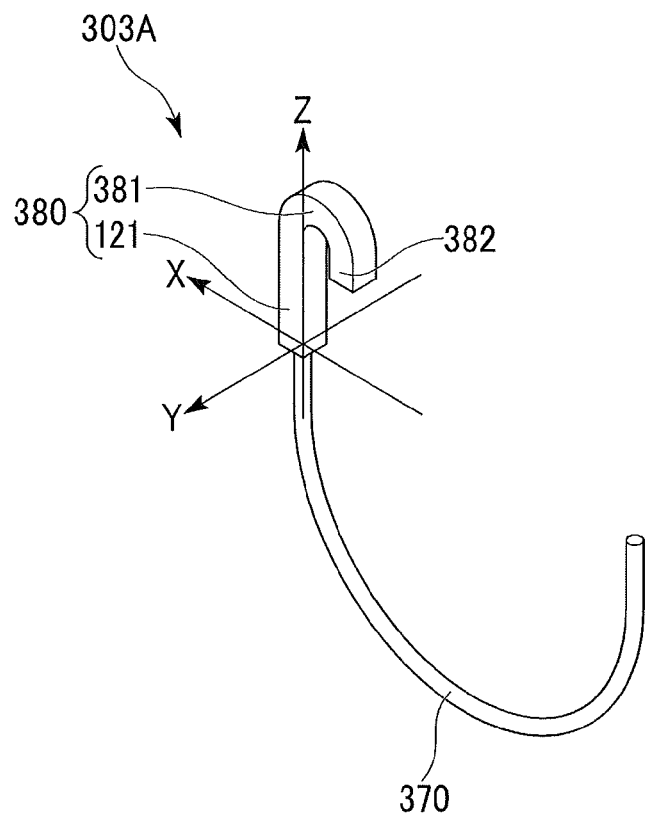
FIG. 20A is a view of a tissue ligating device according to a modified example of the third embodiment of the present invention.
Figure 20B:
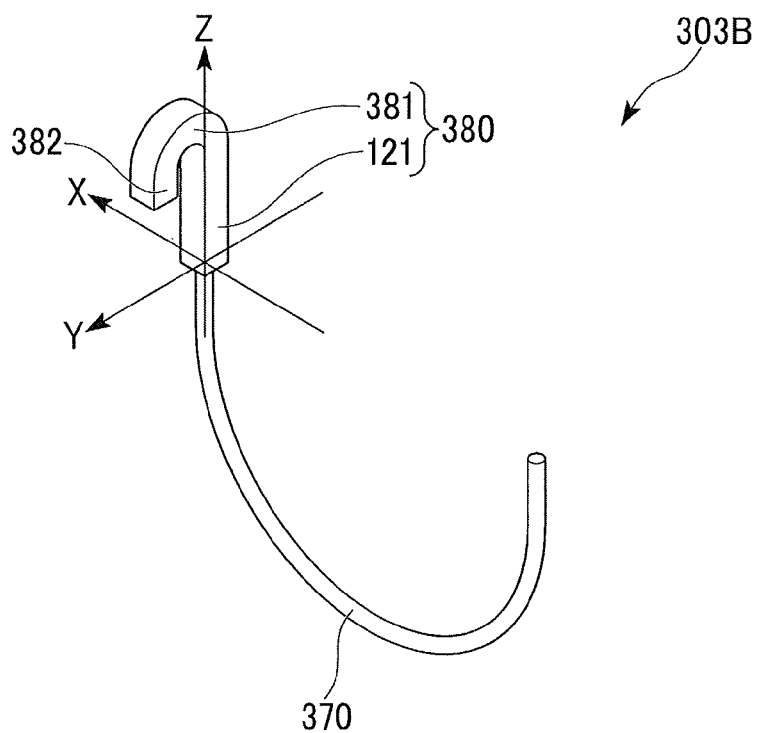
FIG. 20B is a view of a tissue ligating device according to another modified example of the third embodiment of the present invention.

Furthermore, in the device 303 according to the third embodiment of the present invention, as illustrated in FIG. 15 and FIG. 16, the suture 370 is disposed on a side of the positive direction of the X axis, and the groove portion 382 is disposed in a side of the positive direction. However, the present embodiment of the invention is not limited thereto. For example, as a device 303A illustrated in FIG. 20A, the groove portion 382 may be disposed further in the negative direction of the X axis. In addition, as a device 303B illustrated in FIG. 20B, the groove portion 382 may be disposed further in the positive direction of the Y axis on the ZY plane. Even though having the configuration of the device 303A illustrated in FIG. 20A or the configuration of the device 303B illustrated in FIG. 20B, it is possible to obtain the same effects as the device 303 according to the third embodiment.

Fourth Embodiment

Hereinafter, a tissue ligating device (hereinafter referred to as a "device") according to a fourth embodiment of the present invention will be described with reference to FIGS. 21A to 27B.

Figure 21A:
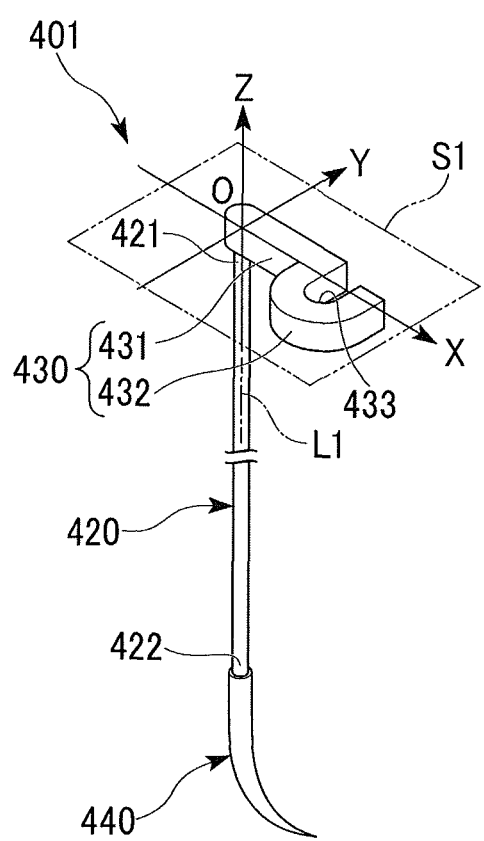
FIG. 21A is a perspective view of a tissue ligating device according to a fourth embodiment of the present invention.
Figure 21B:
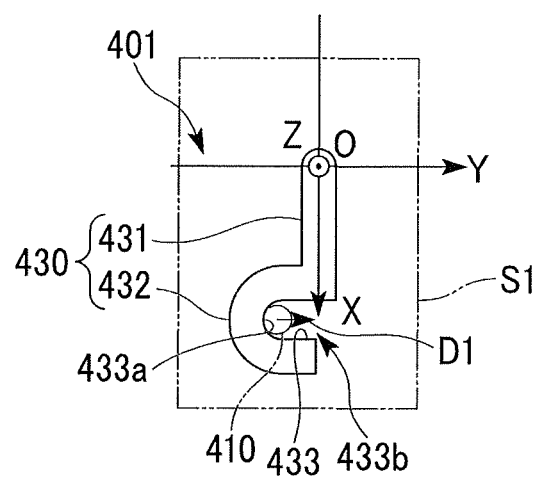
FIG. 21B is a plane view of the tissue ligating device according to the fourth embodiment of the present invention.

As illustrated in FIGS. 21A and 21B, a device 401 includes a suture 420, a hook-shaped member 430 connected to a first end 421 of the suture 420 and a suture needle 440 connected to a second end 422 of the suture 420.

In the present embodiment, the suture 420 is formed of polypropylene. In the suture 420, the elastic modulus and the cross-sectional shape of the suture 420 are adjusted so as to exert an elastic restoring force that balances gravity acting on the hook-shaped member 430 (that lifts the hook-shaped member 430). Meanwhile, the elastic restoring force referred to here means a force whereby the suture will return to its original shape when a suture of any shape is deformed. In other words, it is the force generated in an elastically deformed suture.

It is preferable that the elastic restoring force of the suture 420 is great within a range not impeding the operator's manipulation. The suture 420 is configured such that the elastically deformable distortion range becomes relatively large.

As the material forming the suture 420, a resin or a metal may be suitably used in addition to polypropylene.

Resins that can be used in the suture 420 are classified into absorbent resins and nonabsorbent resins. The absorbent resins include PGA, PLA, PDS, TMC, poly-epsilon-caprolactone and a copolymer thereof. The nonabsorbent resins include nylon, polyester, polypropylene, polybutester, fluorine resin and PET or the like.

On the other hand, as an example of the metal used for the suture 420, stainless steel, a Co—Cr alloy, β titanium, nickel titanium, pure Ti, a Ti alloy, a Mg alloy or the like can be included.

Meanwhile, it is preferable that the mass of the hook-shaped member 430 is about 5 g or less for skin suturing or the like and about 0.01 g or less for a finer area as cardiovascular surgery or the like.

The hook-shaped member 430 includes a straight portion 431 of which a first end portion is connected to the first end 421 of the suture 420 and extends in a straight-line shape, and a bent portion 432 formed at a second end portion opposite to the first end portion of the straight portion 431 to which the suture 420 is connected.

Meanwhile, if the hook-shaped member 430 and the suture 420 are the same in material, they may be integrally configured.

Hereinafter, for the convenience of description, taking the first end 421 of the suture 420 as an origin O, the central axis line in the origin O of the suture 420 is defined as a reference line L1.

The Z axis is defined on the reference line L1, and the direction separating from the suture 420 is taken as a positive direction of the Z axis.

By defining the reference plane S1 that passes the origin O and is orthogonal to the reference line L1, a rectangular coordinate system of the right hand system is defined with the X axis and Y axis arranged on the reference plane S1 and the above-mentioned Z axis.

In the rectangular coordinate system XYZ defined as this, the straight portion 431 extends in the orthogonal direction to the reference line L1, namely, in the positive direction of the X axis. In this case, the derivation direction in which the suture 420 is derived is defined as a negative direction of the Z axis.

A fixing hole, which is not shown, is formed in the first end portion of the straight portion 431. The straight portion 431 is connected to the suture 420 by pressing the first end 421 of the suture 420 into the fixing hole and fixing the first end 421 and the straight portion 431 with an adhesive agent or by welding.

A bent portion 432 is formed in a substantial U shape and is disposed on a reference plane S1, which is the XY plane. A groove portion 433 which can engage a suture 420 is formed in the bent portion 432. The groove portion 433 passes through the bent portion 432 in the direction of the Z axis. The direction D1 facing the opening 433b of the groove portion 433 from the bottom portion 433a of the groove portion 433 is set in the positive direction of the Y axis.

The depth of the groove portion 433 (the distance from the bottom portion 433a to the opening 433b of the groove portion 433) is set larger than the outer diameter of the suture 420.

In the present embodiment, the straight portion 431 and the bent portion 432 are formed integrally by bending-processing a wire formed of stainless steel. The hook-shaped member 430 is formed more solidly than the suture 420, so it can be plastically deformed by caulking.

The cross-sectional shape of the straight portion 431 defined by the plane orthogonal to the axial line on which the straight portion 431 is extended and the cross-sectional shape of the bent portion 432 defined by the plane orthogonal to the axial line on which the bent portion 432 is bent are formed in equivalent rectangular shapes to each other.

The size of the hook-shaped member 430 is preferably about 10 mm or less in the case of skin suturing, for example, and preferably about 2 mm or less in a fine area such as cardiovascular surgery. It is formed to be a considerably small.

Various well-known needles may be used for the suture needle 440, such as a straight-line shaped needle, a bent shaped needle, and a needle of which only a distal end portion is bent and the other portion is formed in a straight-line shape may be chosen suitably considering the suturing portion. There are no particular limitations to the connection aspect of the suture 420 and the suture needle 440. Specifically, the method includes adhesion, fusion, or passing the end portion of the suture 420 through the hole formed in the end portion of the suture needle 440 and tying the suture 420.

Next, the operation using the device 401 configured as above will be described by taking the case of suturing the lacerated wound portion formed on the surface of a tissue as an example.

Figure 22:
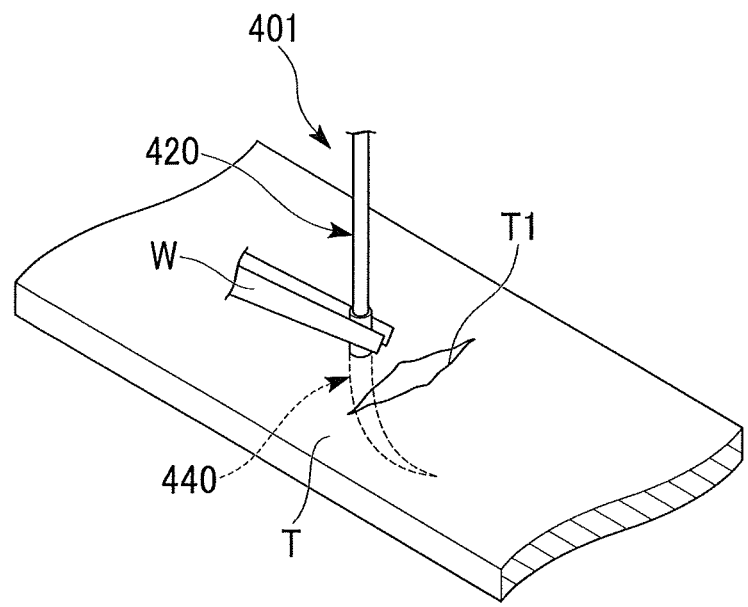
FIG. 22 is a view for describing an operation for suturing a tissue using the tissue ligating device according to the fourth embodiment of the present invention.

First, the operator grasps the suture needle 440 of the device 401 with a grasping forceps W, for example, as shown in FIG. 22 and punctures a portion near a lacerated wound portion T1 of the tissue T with the suture needle 440.

Figure 23:
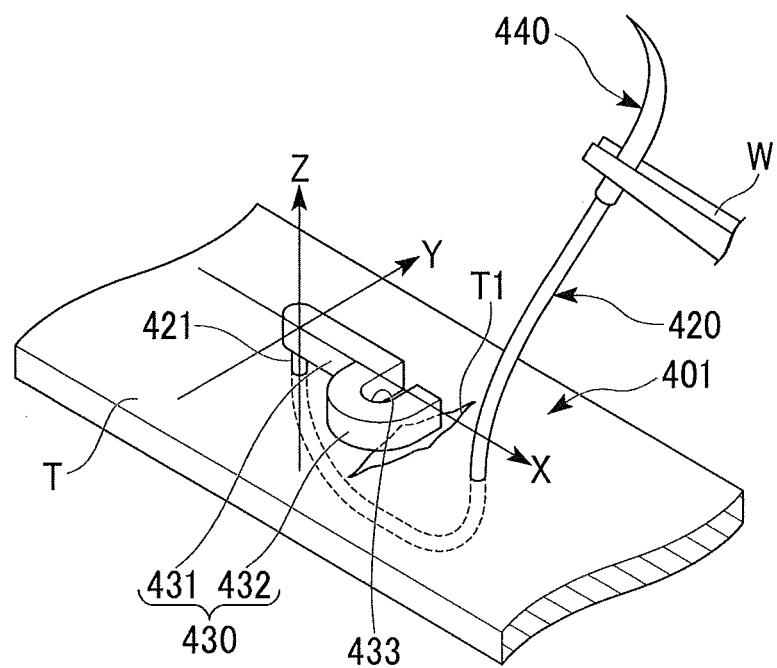
FIG. 23 is a view for describing the operation for suturing the tissue using the tissue ligating device according to the fourth embodiment of the present invention.

As shown in FIG. 23, the operator passes the suture needle 440 and the suture 420 into the tissue T so as to encircle the lacerated wound portion T1. By pulling the suture needle 440 protruding from the tissue T so as to be separated from the lacerated wound portion T1, the first end 421 of the suture 420 is made to protrude from the tissue T as much as the height suitable for the hook-shaped member 430 to be hooked on the suture 420. The height to which the first end 421 protrudes is preferably about several mm to about several cm, for example.

As illustrated in FIG. 23, the suture needle 440 and the suture 420 are passed through the tissue T so as to encircle the lacerated wound portion T1. By pulling the suture needle 440 protruding from the tissue T so as to be separated from the lacerated wound portion T1, the first end 421 of the suture 420 is adjusted to protrude about several mm from the tissue T.

At this time, because the suture 420 can exert the above-mentioned elastic restoring force, the hook-shaped member 430 that is supported by the first end 421 of the suture 420 is kept separated from the tissue T without falling over the tissue T as the hook-shaped member 430 is affected by gravity.

Figure 24:
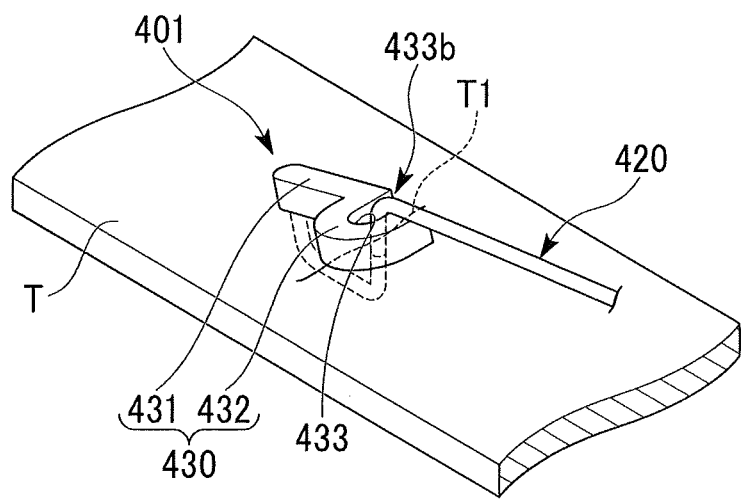
FIG. 24 is a view for describing the operation for suturing the tissue using the tissue ligating device according to the fourth embodiment of the present invention.

The grasping forceps W that grasps the suture needle 440 is moved toward the hook-shaped member 430, and the suture 420 is engaged in the groove portion 433 through the opening 433b as illustrated in FIG. 24 to form a loop with the suture 420. While maintaining the state in which the suture 420 is engaged in the hook-shaped member 430, the suture needle 440 is pulled so as to be separated from the lacerated wound portion T1. Accordingly, the suture 420 is moved in the groove portion 433 so that the hook-shaped member 430 abuts the tissue T1, and the tissue T in the periphery of the lacerated wound portion T1 is constricted by the suture 420, so that the opening of the lacerated wound portion T1 is closed.

Figure 25:
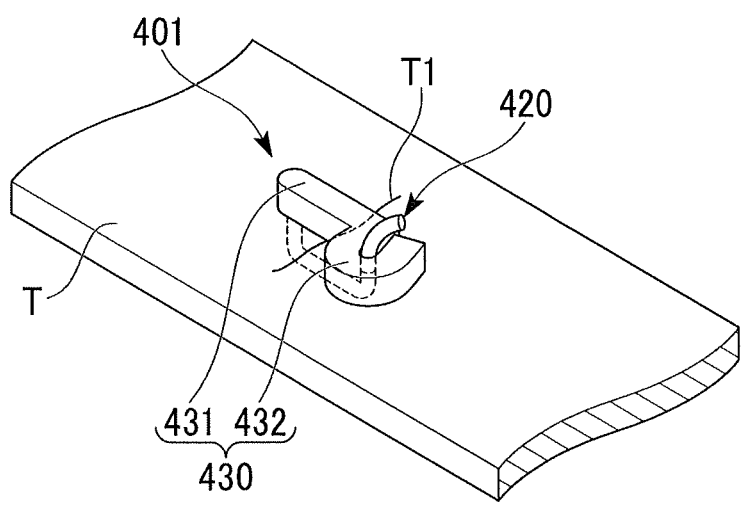
FIG. 25 is a view for describing the operation for suturing the tissue using the tissue ligating device according to the fourth embodiment of the present invention.

With the suture needle 440 pulled so as to be separated from the lacerated wound portion T1, the bent portion 432 of the hook-shaped member 430 is caulked with another grasping forceps, which is not shown, so as to collapse from outside, and the hook-shaped member 430 is fixed to the suture 420, as shown in FIG. 25. Thus, the tissue T is ligated by forming a knot with the suture 420 and the caulked hook-shaped member 430.

The suture 420 is cut at the side closer to the suture needle 440 than the caulked hook-shaped member 430 with a medical knife, and the suture needle 440 and the cut suture 420 are removed to end the manipulation.

As described above, in the device 401 according to the present embodiment, when the suture 420 is made to pass through the tissue T from the second end 422, the first end 421 of the suture 420 is made to protrude from the tissue T, so that the hook-shaped member 430 is kept separated from the tissue T by the elastic restoring force of the suture 420. By engaging the suture 420 that has passed through the tissue T in the groove portion 433 of the hook-shaped member 430 that is separated from the tissue T, it is possible to engage the suture 420 in the hook-shaped member 430 easily.

Since the device 401 is provided with the suture needle 440, it is possible to make the suture 420 connected to the suture needle 440 pass through the tissue T easily.

The shape of the device 401 according to the present embodiment can be modified variously as will be described below.

Figure 26A:
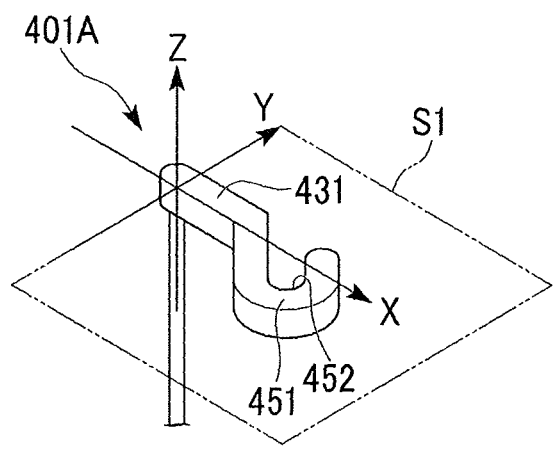
FIG. 26A is a perspective view of major parts of a tissue ligating device according to a modified example of the fourth embodiment of the present invention.
Figure 26B:
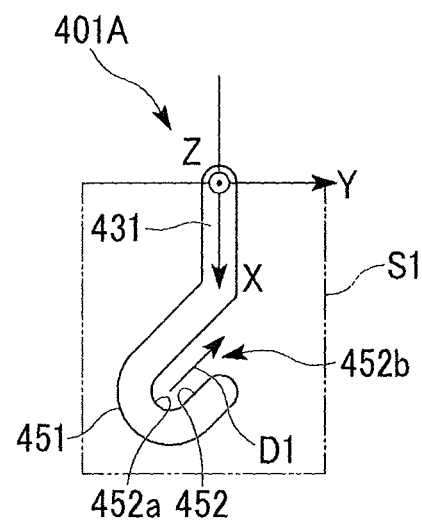
FIG. 26B is a plane view of the major parts of the tissue ligating device according to the modified example of the fourth embodiment of the present invention.

For example, as the device 401A illustrated in FIGS. 26A and 26B, a bent portion 451 in which a groove portion 452 is formed may be provided, instead of the bent portion 432 of the device 401 of the fourth embodiment.

The bent portion 451 is formed in a substantial U shape and is disposed on the reference plane S1, which is the XY plane. The direction D1 facing the opening 452b from the bottom portion 452a of the groove portion 452 is set in the direction between the negative direction of the X axis and the positive direction of the Y axis. In the bent portion 451 formed in a substantial U shape, the end portion on a side of the negative direction of the X axis is connected to the straight portion 431, and the opening 452b of the groove portion 452 is disposed on a nearer side of the positive direction of the X axis than the connection portion of the straight portion 431 and the bent portion 451. The straight portion 431 and the bent portion 451 are integrally formed of the same material as the hook-shaped member 430.

Figure 27A:
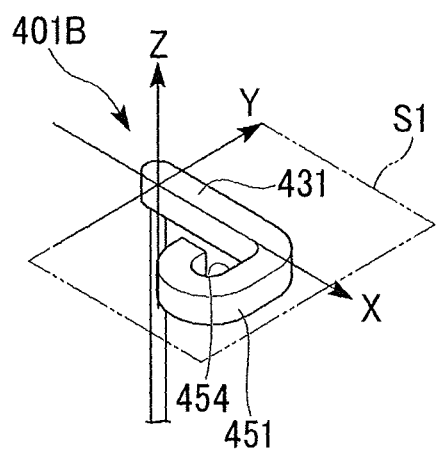
FIG. 27A is a perspective of the major parts of the tissue ligating device according to the modified example of the fourth embodiment of the present invention.
Figure 27B:
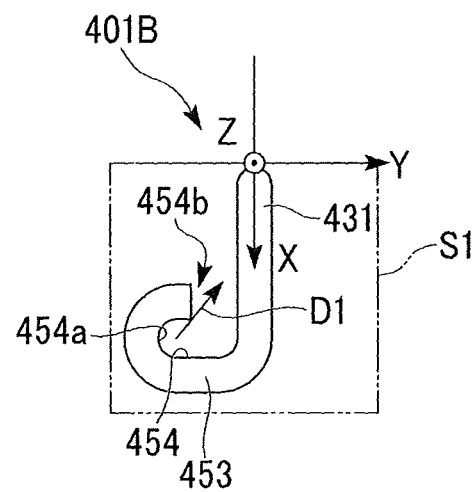
FIG. 27B is a plane view of the major parts of the tissue ligating device according to the modified example of the fourth embodiment of the present invention.

The device 401B illustrated in FIGS. 27A and 27B includes a bent portion 453 in which a groove portion 454 is formed, instead of the bent portion 432 of the device 401 of the fourth embodiment.

The bent portion 453 is formed in a substantial J shape and is disposed on the reference plane S1. The direction D1 facing the opening 454b from the bottom portion 454a of the groove portion 454 is set in the direction between the negative direction of the X axis and the positive direction of the Y axis. In the bent portion 453 formed in a substantial J shape, the end portion on a side of the positive direction of the Y axis is connected to the straight portion 431.

The opening 454b of the groove portion 454 is disposed on a nearer side of the negative direction of the Y axis than the connection portion of the straight portion 431 and the bent portion 453.

Because the bent portion is kept separated from the tissue T by the elastic restoring force of the suture 420, as in the device 401 according to the present embodiment, it is possible to engage the suture 420 in the hook-shaped member 430 easily even in the devices 401A and 401B configured as above.

Figure 28:
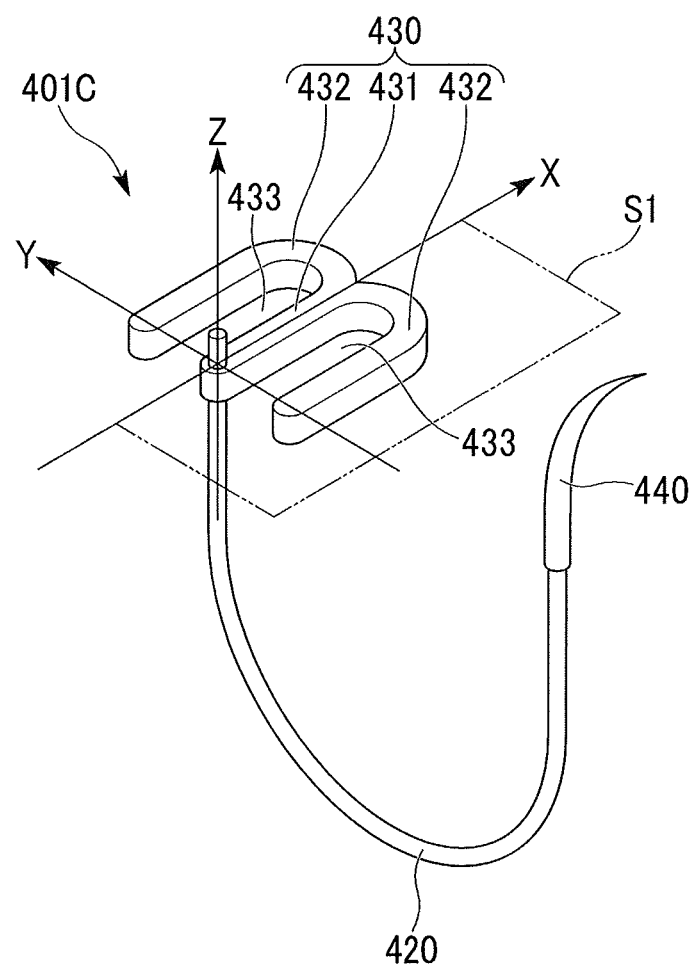
FIG. 28 is a view of a tissue ligating device according to a combination of the third embodiment and the forth embodiment of the present invention.

Further, the device 404 may be combined with the configuration according to the third embodiment of the present invention. FIG. 28 shows a device 401C in which a device 401 is combined with the device according to third embodiment of the present invention. In the device 401C, the straight portion 431 extends in a positive direction of X axis. The device 401C includes two bent portions 432 formed in a substantial U shape. Two bent portions 432 are disposed on a reference plane S1, which is a XY plane, and on two sides of the straight portion 431, respectively. That is, on the reference plane S1, one bent portion 432 is disposed on a side of the Y axis in the positive direction of the Y axis and so as to sandwich the straight portion 431 extending in the positive direction of the X axis, and the other bent portion 432 is disposed on a side of the Y axis in the negative direction of the Y axis. By being configured above, in addition to obtain effects of the forth embodiment of the present invention, it is possible to engage the suture 420 in the hook-shaped member 430 easily.

Fifth Embodiment

Next, a fifth embodiment of the present invention will be described with reference to FIGS. 29A to 31. The same parts as in the above-mentioned embodiments will be denoted by the same reference numerals, a description thereof will be omitted here, and only differences will be described.

Figure 29A:
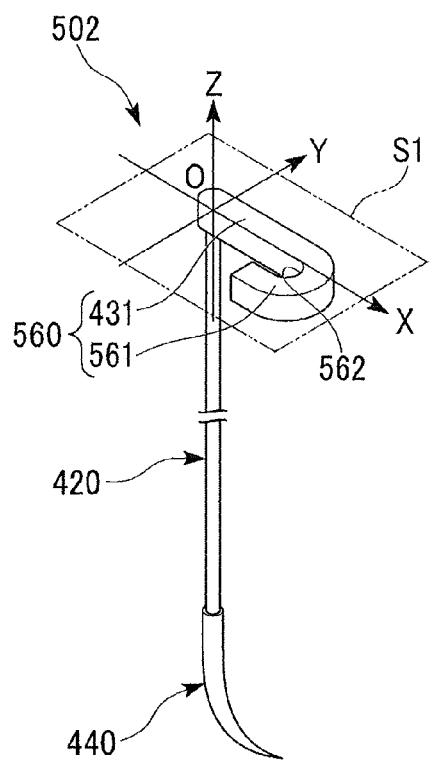
FIG. 29A is a perspective view of a tissue ligating device according to a fifth embodiment of the present invention.
Figure 29B:
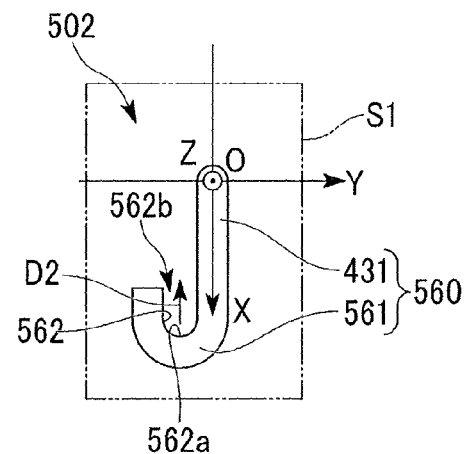
FIG. 29B is a plane view of the tissue ligating device according to the fifth embodiment of the present invention.

As illustrated in FIGS. 29A and 29B, a device 502 according to the present embodiment includes a hook-shaped member 560 instead of the hook-shaped member 430 of the device 401 of the fourth embodiment.

The hook-shaped member 560 includes the above-mentioned straight portion 431 and a bent portion 561 in which a groove portion 562 is formed.

The bent portion 561 is formed in a substantial U shape and is disposed on the reference plane S1. The groove portion 562 is formed in such a way that the direction D2 facing the opening 562b of the groove portion 562 from the bottom portion 562a of the groove portion 562 becomes substantially parallel (the negative direction of the X axis) to the straight portion 431 and faces the first end portion of the straight portion 431 to which the suture 420 is connected. The groove portion 562 is formed on a side of the negative direction of the Y axis with respect to the straight portion 431.

The inner wall surface of the groove portion 562 is continued into (directly connected) the outer peripheral surface of the straight portion 431.

Next, the operation using the device 502 configured as above will be described by taking the case of suturing the lacerated wound portion T1 formed on the surface of the tissue T as an example.

Since the operation is identical to the case of using the device 401 of the fourth embodiment and the process performed until the hook-shaped member 560 is kept separated from the tissue T, the sequence after that will be described.

Figure 30:
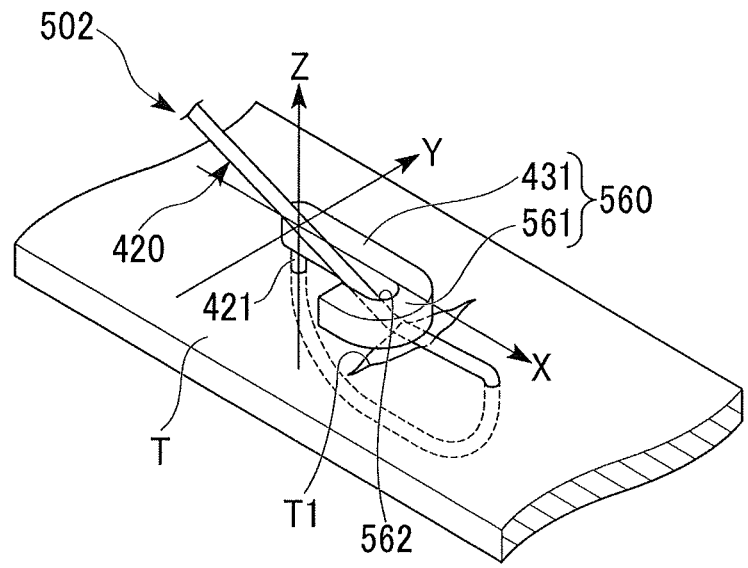
FIG. 30 is a view for describing an operation for suturing a tissue using the tissue ligating device according to the fifth embodiment of the present invention.

The operator moves the grasping forceps W that grasps the suture needle 440 such that the middle portion of the suture 420 abuts the first end portion of the straight portion 431 to which the suture 420 is connected, as illustrated in FIG. 30. If the force that maintains the position of the second end 422 of the suture 420 by the grasping forceps W is weakened, the suture 420 is deformed by its own elastic restoring force so as to widen the formed loop. Accordingly, the middle portion of the suture 420 is moved along the straight portion 431 so as to be separated from the first end 421 of the suture 420, and the suture 420 is engaged in the groove portion 562.

Figure 31:
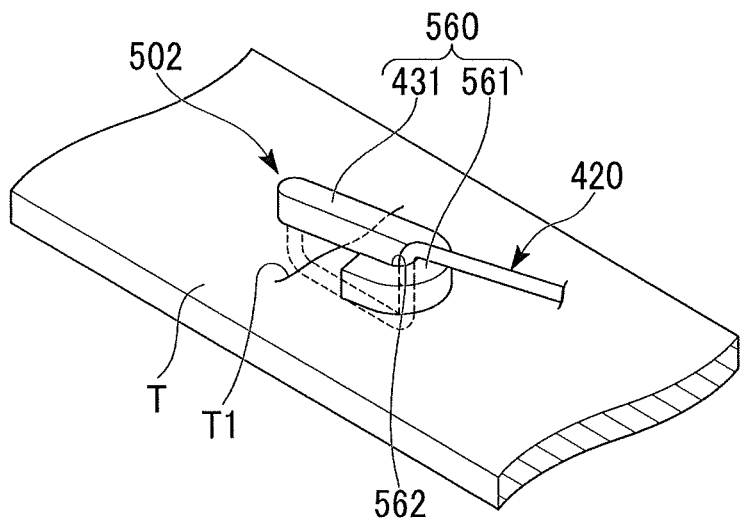
FIG. 31 is a view for describing the operation for suturing the tissue using the tissue ligating device according to the fifth embodiment of the present invention.

As illustrated in FIG. 31, with the suture 420 engaged in the hook-shaped member 560, the grasping forceps W is pulled so as to be separated from the lacerated wound portion T1. Accordingly, the tissue T in the periphery of the lacerated wound portion T1 is constricted by the suture 420. The bent portion 561 of the hook-shaped member 560 is caulked with another grasping forceps or the like, which is not shown, and the hook-shaped member 560 is fixed to the suture 420. The suture 420 is cut nearer the second end 422 than the fixed hook-shaped member 560, and the manipulation is ended.

As described above, in the device 502 according to the present embodiment, by moving the middle portion of the suture 420 abutting the side of the first end portion of the straight portion 431 to which the suture 420 is connected so as to slide along the straight portion 431, it is possible to engage the suture 420 in the groove portion 562 more easily.

If the force that maintains the position of the second end 422 of the suture 420 by the grasping forceps W is weakened, the suture 420 can be automatically engaged in the groove portion 562 by the elastic restoring force of the suture 420.

Further, because the opening 562b of the groove portion 562 is formed so as to face the side of the first end portion of the straight portion 431 to which the suture 420 is connected, the operator can easily recognize the direction D2 of the opening 562b.

Sixth Embodiment

Next, a sixth embodiment according to the present invention will be described with reference to FIGS. 32 to 39. The same parts as in the above-mentioned embodiments will be denoted by the same reference numerals, a description thereof will be omitted here, and only differences will be described.

Figure 32:
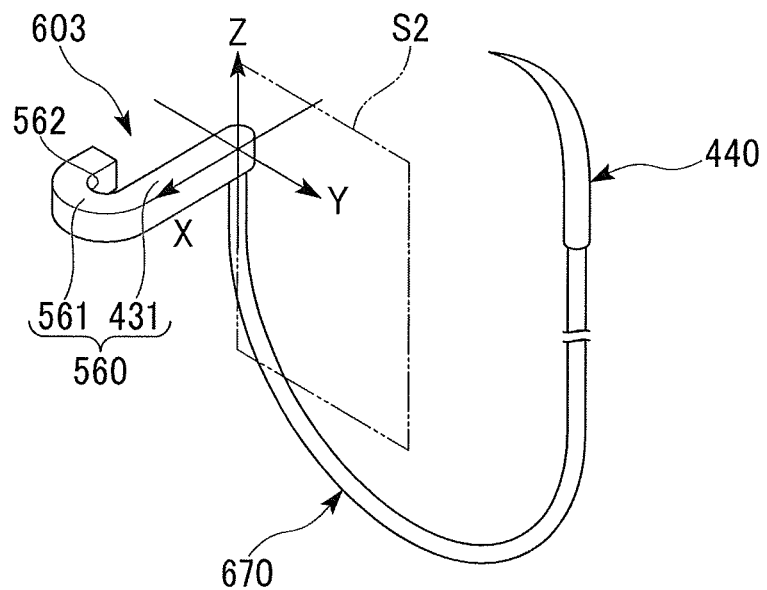
FIG. 32 is a perspective view of a tissue ligating device according to a sixth embodiment of the present invention.
Figure 33:
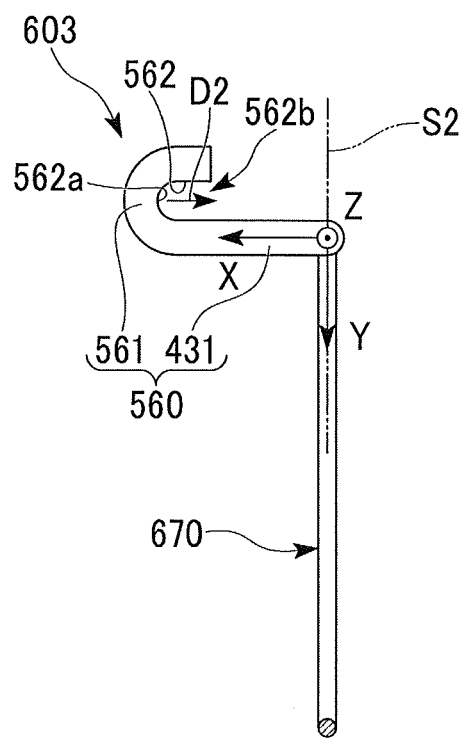
FIG. 33 is a plane view in which a portion of the tissue ligating device according to the sixth embodiment of the present invention is broken out.

As illustrated in FIGS. 32 and 33, a device 603 according to the present embodiment includes a suture 670 instead of the suture 420 of the device 502 of the fifth embodiment.

The groove portion 562 is formed in such a way that the direction D2 facing the opening 562b from the bottom portion 562a of the groove portion 562 intersects the curved reference plane S2.

The suture 670 is formed in a bent shape, in which its own middle portion becomes convex in a natural state in the negative direction of the Z axis on the curved reference plane S2 that becomes the YZ plane. In the present embodiment, the suture 670 is bent about 180 degrees at the central angle. Both end portions of the suture 670 are formed in a straight-line shape extending substantially parallel with the Z axis. For the suture 670, a comparatively solid resin such as polypropylene may be suitably used. The shape of the suture 670 that is bent in a natural state can be formed by, for example, heat treating the suture 670. Meanwhile, a resin for the material forming the suture 670 is not limited to polypropylene, and a nonabsorbent resin such as nylon, polyester, polypropylene, polybutester, fluorine resin, or PET, and an absorbent resin such as PGA, PLA, PDS, TMC, poly-epsilon-caprolactone and a polymer thereof may be used. For the suture 670, a metal such as stainless steel, a Co—Cr alloy, β titanium, nickel titanium, pure Ti, a Ti alloy, or a Mg alloy may be used. When the suture 670 is formed of stainless steel or the like, the shape of the suture 670 that is bent in the natural state may be formed by quenching or the like.

In the present embodiment, the straight portion 431 extends in the direction orthogonal to the YZ plane, that is, in the positive direction of the X axis.

Next, the operation when using the device 603 configured as above will be described.

Since the operation is identical to the case of using the device 401 of the fourth embodiment and the process performed until the hook-shaped member 560 is holded so as to be floated from the tissue T, the sequence after that will be described.

Meanwhile, because the suture 670 is formed in a bent shape, the straight portion 431 is disposed so as to extend in the positive direction of the X axis, that is, so as to be orthogonal to the curved reference plane S2, with respect to the YZ plane defined by the suture 670, when the suture needle 440 is passed through so as to encircle the lacerated wound portion T1. The groove portion 562 is disposed on a side of the negative direction of the Y axis with respect to the straight portion 431.

Figure 34:
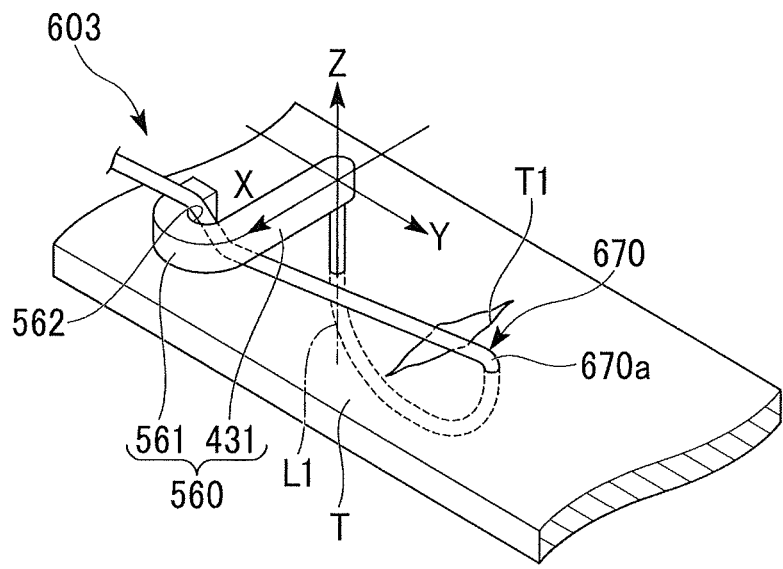
FIG. 34 is a view for describing an operation for suturing a tissue using the tissue ligating device according to the sixth embodiment of the present invention.

The operator engages the suture 670 in the groove portion 562 of the hook-shaped member 560 from the tissue T by moving the grasping forceps W that grasps the suture needle 440, as shown in FIG. 34. At this time, as shown in the bent portion 670a of the suture 670, the suture 670 is bent so that the radius of curvature of the suture 670 becomes relatively small (forms a small loop).

Figure 35:
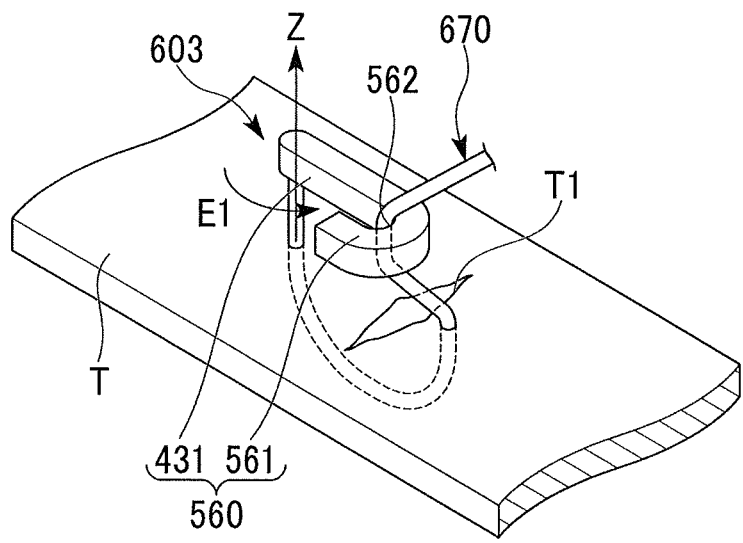
FIG. 35 is a view for describing the operation for suturing the tissue using the tissue ligating device according to the sixth embodiment of the present invention.

With the suture 670 engaged in the hook-shaped member 560, when the grasping forceps W is moved in the positive direction of the Y axis by, for example, weakening the force that maintains the position of the suture 670 by the grasping forceps W, the radius of curvature of the loop of the suture 670 that is formed to be small increases, and the hook-shaped member 560 rotates around the Z axis about 90 degrees in the direction E1 (clockwise as seen in the positive direction of the Z axis), as shown in FIG. 35.

Figure 36:
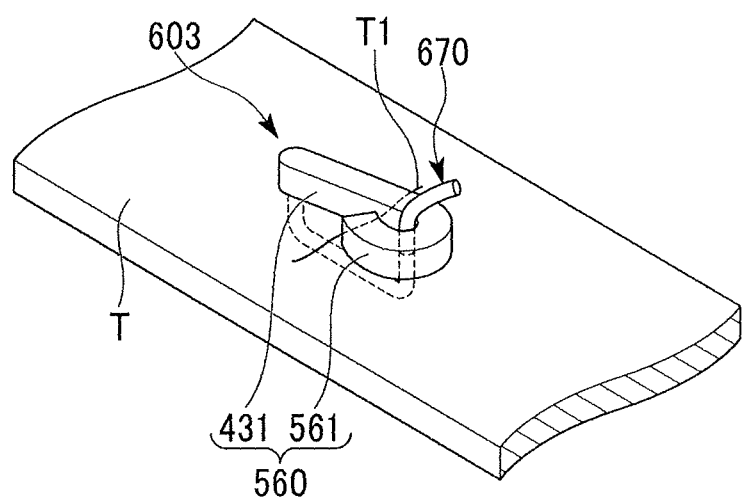
FIG. 36 is a view for describing the operation for suturing the tissue using the tissue ligating device according to the sixth embodiment of the present invention.

If the suture needle 440 is pulled so as to be separated further from the lacerated wound portion T1, the hook-shaped member 560 abuts the tissue T and the tissue T around the lacerated wound portion T1 is constricted by the suture 670, so that the opening of the lacerated wound portion T1 is closed, as shown in FIG. 36.

The bent portion 561 of the hook-shaped member 560 is caulked to fix the hook-shaped member 560 to the suture 670 and a proper portion of the suture 670 is cut with a medical knife to end the manipulation.

As described above, according to the device 603 according to the present embodiment, it is possible to engage the suture 670 in the hook-shaped member 560 easily when suturing the tissue T.

The suture 670 is formed so as to be bent in a natural state. Accordingly, when the suture 670 is passed through the tissue T so as to encircle the lacerated wound portion T1, the direction of the hook-shaped member 560 with respect to the suture 670 is determined. Therefore, it is possible to engage the suture 670 in the groove portion 562 easily even when it is difficult for the operator to confirm the position of the groove portion 562 visually because the hook-shaped member 560 is formed to be considerably small.

Because the groove portion 562 is formed in such a way that the direction D2 intersects the curved reference plane S2, it is possible to engage the suture 670 in the groove portion 562 by moving the suture 670 so as to intersect the curved reference plane S2.

Because the straight portion 431 extends in the direction orthogonal to the YZ plane, the hook-shaped member 560 rotates around the Z axis when the tissue T is constricted. Accordingly, the operator can easily recognize whether the suture 670 is engaged in the hook-shaped member 560 by confirming the rotating motion.

The shape of the device 603 according to the present embodiment can be modified variously as will be described below.

Figure 37:
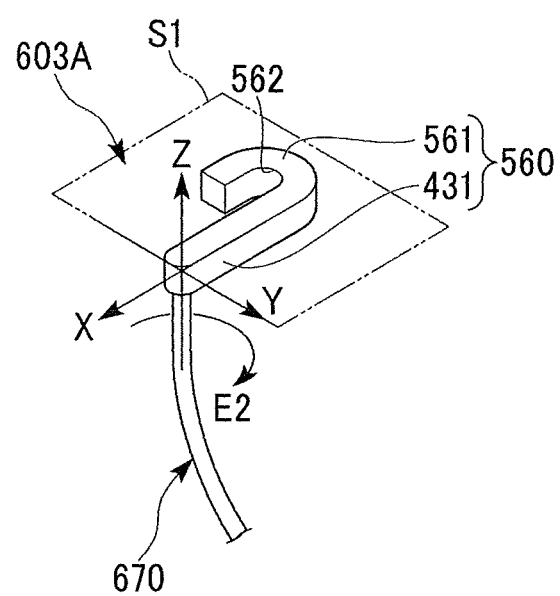
FIG. 37 is a perspective view of major parts of a tissue ligating device according to a modified example of the sixth embodiment of the present invention.

For example, the device 603 according to the present embodiment may be modified as the device 603A illustrated in FIG. 37.

In the device 603A, the straight portion 431 extends in the negative direction of the X axis with respect to the YZ plane defined by the suture 670. The bent portion 561 is formed in a substantial U shape and is disposed on the reference plane S1. The groove portion 562 is formed in a side of the negative direction of the Y axis with respect to the straight portion 431.

In the device 603A configured as above, when the grasping forceps W is moved in the positive direction of the Y axis, with the suture 670 engaged in the hook-shaped member 560, the hook-shaped member 560 rotates around the Z axis about 90 degrees in the direction E2 (counterclockwise as seen in the positive direction of the Z axis).

Other than that, by performing the same sequence as in the device 603 according to the present embodiment, the suture 670 can be easily engaged in the hook-shaped member 560.

Figure 38:
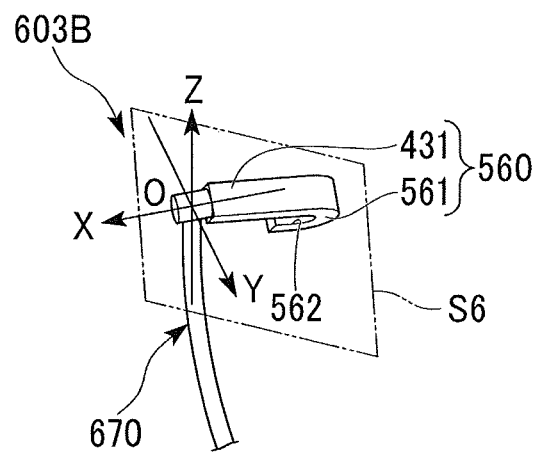
FIG. 38 is a perspective view of the major parts of the tissue ligating device according to the modified example of the sixth embodiment of the present invention.

In the device 603B illustrated in FIG. 38, the straight portion 431 is disposed so as to face the direction between the negative direction of the X axis, the negative direction of the Y axis, and the negative direction of the Z axis. The bent portion 561 is disposed on a plane S6 that passes the origin O, taking the direction between the negative direction of the X axis, the negative direction of the Y axis and the positive direction of the Z axis, as a normal line. The groove portion 562 is formed in a side of the negative direction of the Y axis and in a side of the negative direction of the Z axis with respect to the straight portion 431.

Figure 39:
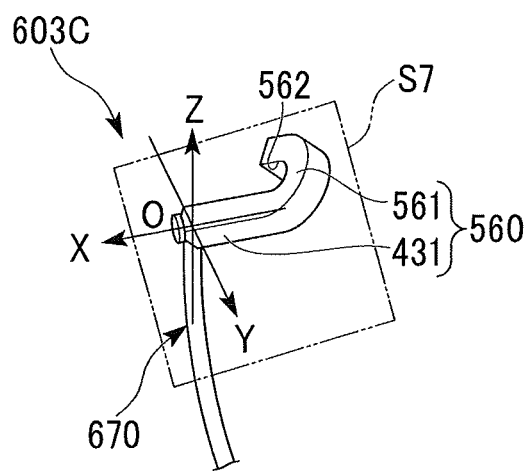
FIG. 39 is a perspective view of the major parts of the tissue ligating device according to the modified example of the sixth embodiment of the present invention.

Further, in the device 603C illustrated in FIG. 39, the straight portion 431 is disposed so as to face the direction between the negative direction of the X axis, the positive direction of the Y axis and the positive direction of the Z axis. The bent portion 561 is disposed on a plane S7 that passes the origin O, taking the direction between the positive direction of the X axis, the negative direction of the Y axis and the positive direction of the Z axis, as a normal line. The groove portion 562 is formed in a side of the negative direction of the Y axis and in a side of the positive direction of the Z axis with respect to the straight portion 431.

Even any one of the devices 603B and 603C, because the groove portion 562 is disposed in the negative direction of the Y axis with respect to the straight portion 431, the suture 670 can be engaged easily in the hook-shaped member 560 by performing the same sequence as the above-mentioned devices 603 and 603A.

Figure 40:
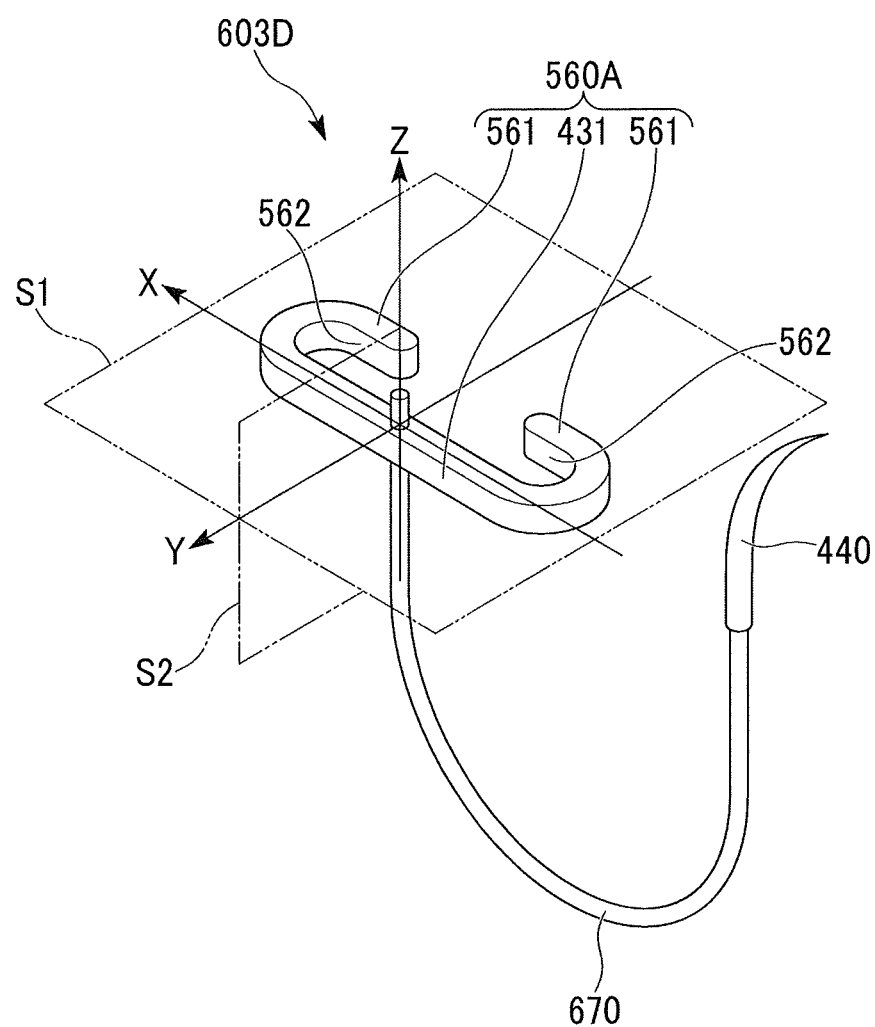
FIG. 40 is a view of a tissue ligating device according to a combination of the fifth embodiment and the sixth embodiment of the present invention.

Further, the device 603 according to the sixth embodiment of the present invention may be combined with the configuration according to the fifth embodiment of the present invention. FIG. 40 shows a device 603D in which a device 603 is combined with the device according to the fifth embodiment of the present invention. The device 603D includes hook-shaped member 560A in which bent portions 561 are respectively provided at both ends of a straight portion 431. The bent portions 561 are formed in a substantial U shape and disposed on the reference plane S1. One bent portion 561 is disposed on a side the positive direction of the X axis of the straight portion 431. The other bent portion 561 is disposed on a side the negative direction of the X axis. Both a groove 562 provided with the one bent portion 561 and a groove portion 562 provided with the other bent portion 561 are formed in a side of the negative direction of the Y axis with respect to the straight portion 431 and formed so as to face each other. A suture 670 is formed in bent shape in which a central portion thereof has convex shape in the negative direction of the Z axis on a curved reference plane S2 which becomes the YZ plane under natural conditions. By being configured above, in addition to obtain effects of the fifth embodiment of the present invention, it is possible to obtain the effect according to the sixth embodiment.

Seventh Embodiment

Next, a seventh embodiment of the present invention will be described with reference to FIGS. 41 to 49. The same parts as in the above-mentioned embodiments will be denoted by the same reference numerals, a description thereof will be omitted here, and only differences will be described.

Figure 41:
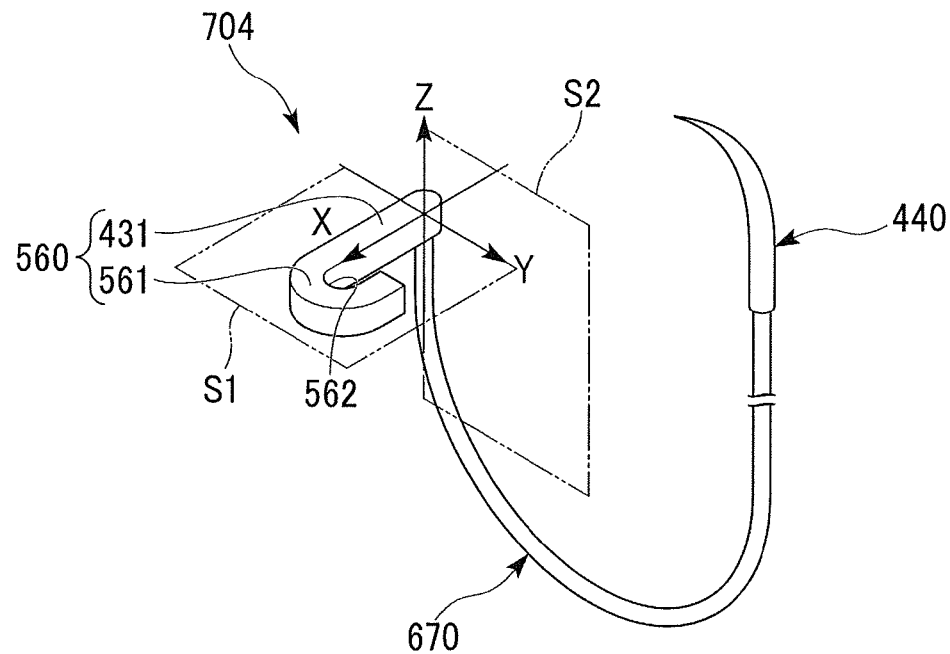
FIG. 41 is a perspective view of a tissue ligating device according to a seventh embodiment of the present invention.
Figure 42:
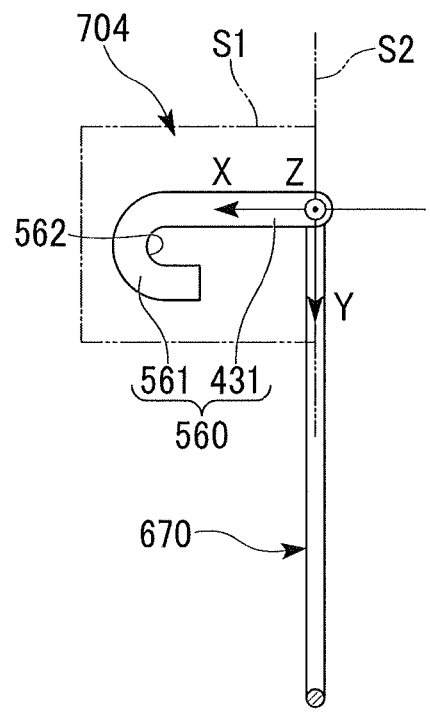
FIG. 42 is a plane view in which a portion of the tissue ligating device according to the seventh embodiment of the present invention is broken out.

As shown in FIGS. 41 and 42, a device 704 according to the present embodiment is different only in that a direction in which the bent portion 561 is connected to the straight portion 431, relative to the device 603 of the sixth embodiment.

The bent portion 561 is disposed on the reference plane S1, which is the XY plane, in such a way that the groove portion 562 is formed in a side of the positive direction of the Y axis with respect to the straight portion 431.

Next, the operation when using the device 704 configured as above will be described.

Since the operation is identical to the case of using the device 401 of the fourth embodiment and the process performed until the hook-shaped member 560 is kept separated from the tissue T, the sequence after that will be described.

Meanwhile, because the suture 670 is formed in a bent shape, the straight portion 431 is disposed so as to extend in a side of the positive direction of the X axis, that is, so as to be orthogonal to the curved reference plane S2 which is a YZ plane, with respect to the YZ plane defined by the suture 670, when the suture needle 440 is passed through so as to encircle the lacerated wound portion T1. The groove portion 562 is disposed on a side of the positive direction of the Y axis with respect to the straight portion 431.

Figure 43:
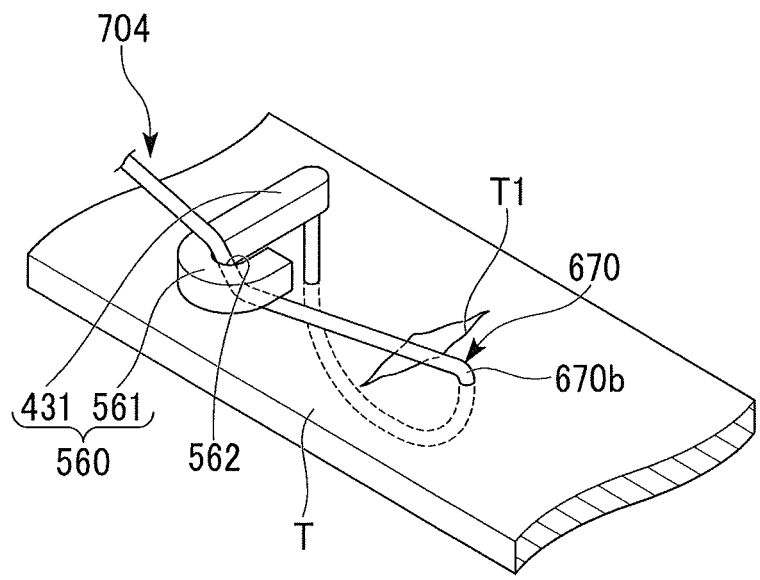
FIG. 43 is a view for describing an operation for suturing a tissue using the tissue ligating device according to the seventh embodiment of the present invention.

The operator engages the suture 670 in the groove portion 562 of the hook-shaped member 560 from the tissue T by moving the grasping forceps W that grasps the suture needle 440, as shown in FIG. 43. At this time, as shown in the bent portion 670*b* of the suture 670, the suture 670 is bent so that the radius of curvature of the suture 670 becomes relatively large (forms a large loop) compared to that of the above-mentioned bent portion 670*a*.

Figure 44:
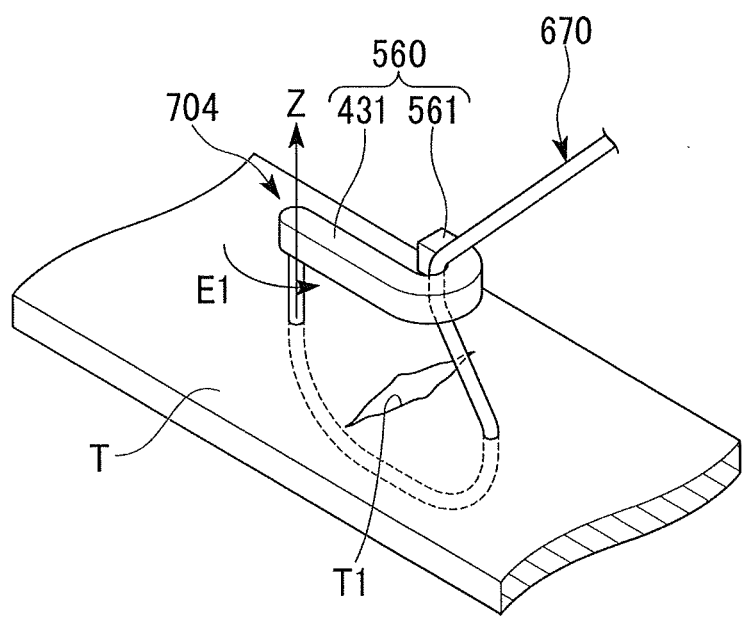
FIG. 44 is a view for describing the operation for suturing the tissue using the tissue ligating device according to the seventh embodiment of the present invention.

With the suture 670 engaged in the hook-shaped member 560, when the grasping forceps W is moved in a side of the positive direction of the Y axis, the radius of curvature of the loop of the suture 670 increases and the hook-shaped member 560 rotates around the Z axis about 90 degrees in the direction E1, as shown in FIG. 44.

Figure 45:
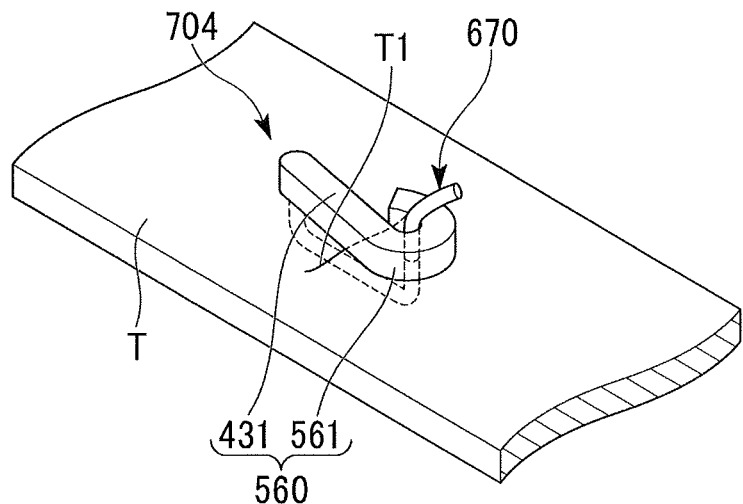
FIG. 45 is a view for describing the operation for suturing the tissue using the tissue ligating device according to the seventh embodiment of the present invention.

If the suture needle 440 is drawn out so as to be separated further from the lacerated wound portion T1, the hook-shaped member 560 abuts the tissue T and the tissue T around the lacerated wound portion T1 is constricted by the suture 670, so that the opening of the lacerated wound portion T1 is closed, as shown in FIG. 45.

The operation after this is the same as the case of using the above device 401, so a description will be omitted here.

As described above, in the device 704 according to the present embodiment, it is possible to bring about the same effect as the device 603 in the above embodiment.

Figure 46:
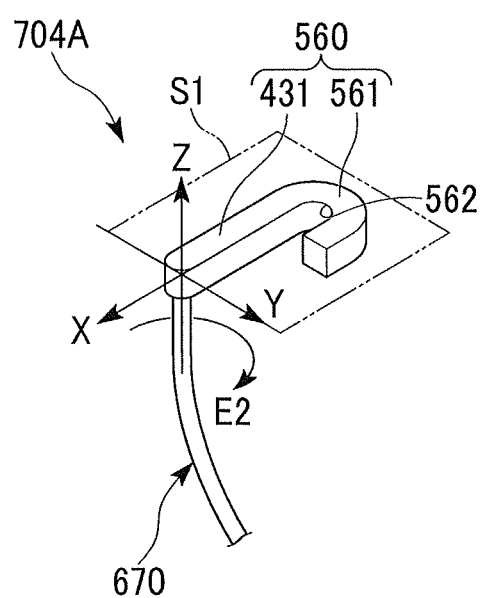
FIG. 46 is a perspective view of major parts of a tissue ligating device according to a modified example of the seventh embodiment of the present invention.

In addition, the device 704 according to the present embodiment may be modified as a device 704A illustrated in FIG. 46.

In the device 704A, the straight portion 431 extends in the negative direction of the X axis with respect to the YZ plane defined by the suture 670. The bent portion 561 is formed in a substantial U shape and is disposed on the reference plane S1. The groove portion 562 is formed in a side of the positive direction of the Y axis with respect to the straight portion 431.

According to the device 704A configured as above, when the grasping forceps W is moved in the positive direction of the Y axis, with the suture 670 engaged in the hook-shaped member 560, the hook-shaped member 560 rotates around the Z axis about 90 degrees in the direction E2.

Other than that, by performing the same sequence as the device 704 according to the present embodiment, the suture 670 can be easily engaged in the hook-shaped member 560.

Figure 47:
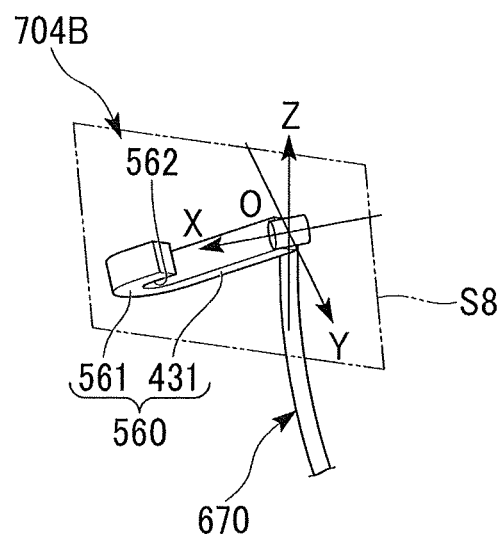
FIG. 47 is a perspective view of the major parts of the tissue ligating device according to the modified example of the seventh embodiment of the present invention.

In a device 704B illustrated in FIG. 47, the straight portion 431 is disposed so as to face the direction between the positive direction of the X axis, the negative direction of the Y axis, and the negative direction of the Z axis. The bent portion 561 is disposed on a plane S8 that passes the origin O, taking the direction between the positive direction of the X axis, the negative direction of the Y axis and the positive direction of the Z axis, as a normal line. The groove portion 562 is formed in a side of the positive direction of the Y axis and in a side of the positive direction of the X axis with respect to the straight portion 431.

Figure 48:
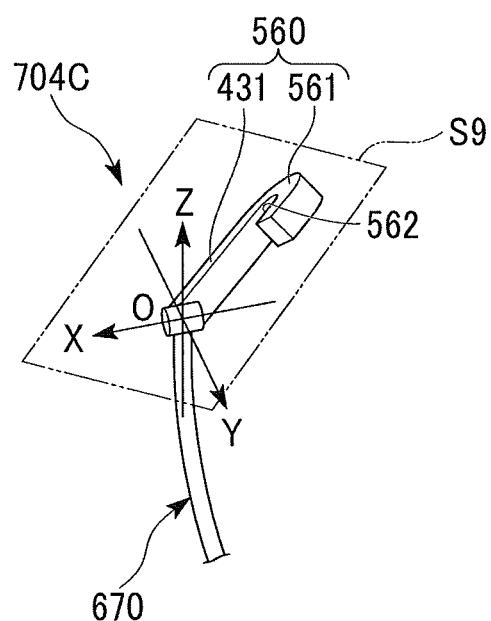
FIG. 48 is a perspective view of the major parts of the tissue ligating device according to the modified example of the seventh embodiment of the present invention.

In a device 704C illustrated in FIG. 48, the straight portion 431 is disposed so as to face the direction between the negative direction of the X axis, the negative direction of the Y axis and the positive direction of the Z axis. The bent portion 561 is disposed on a plane S9 that passes the origin O, taking the direction between the positive direction of the X axis, the positive direction of the Y axis and the positive direction of the Z axis, as a normal line. The groove portion 562 is formed in a side of the positive direction of the Y axis with respect to the straight portion 431.

Figure 49:
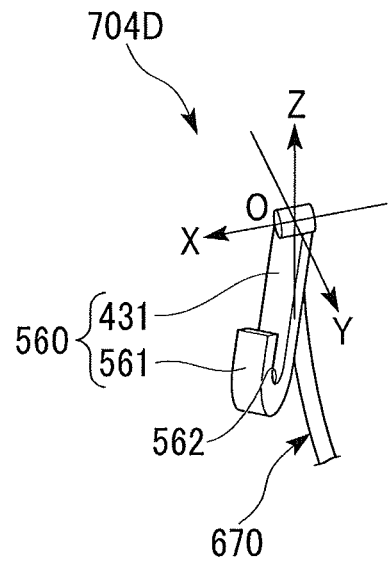
FIG. 49 is a perspective view of the major parts of the tissue ligating device according to the modified example of the seventh embodiment of the present invention.

Further, in a device 704D illustrated in FIG. 49, the straight portion 431 is disposed so as to face the direction between the positive direction of the X axis, the positive direction of the Y axis and the negative direction of the Z axis. The bent portion 561 is disposed on a plane that passes the origin O, taking the direction between the positive direction of the X axis, the positive direction of the Y axis and the positive direction of the Z axis, as a normal line. The groove portion 562 is formed in a side of the positive direction of the Y axis and in a side of the positive direction of the X axis with respect to the straight portion 431.

Even in any one of the devices 704B, 704C and 704D, it is possible to engage the suture 670 in the hook-shaped member 560 easily by performing the same sequence as in the above-mentioned devices 704 and 704A.

Eighth Embodiment

Next, an eighth embodiment of the present invention will be described with reference to FIGS. 50 to 54. The same parts as in the above-mentioned embodiments will be denoted by the same reference numerals, a description thereof will be omitted here, and only differences will be described.

Figure 50:
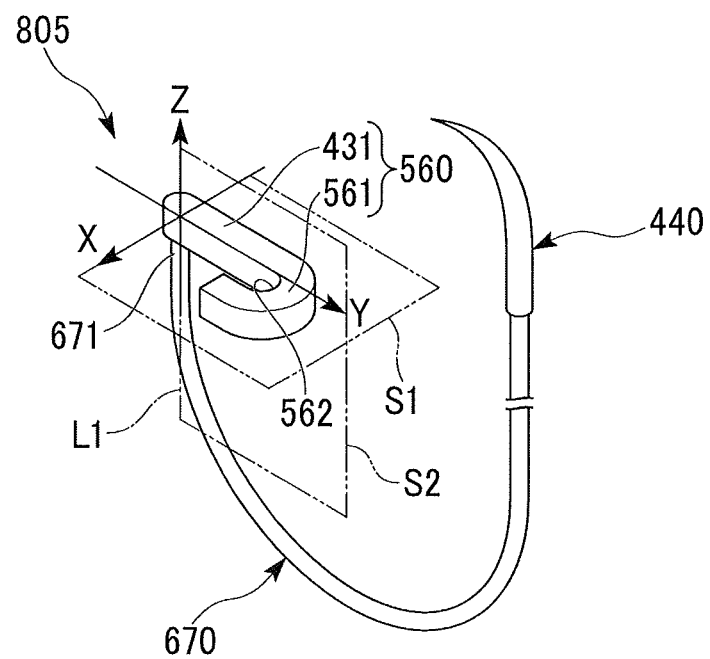
FIG. 50 is a perspective view of a tissue ligating device according to an eighth embodiment of the present invention.
Figure 51:
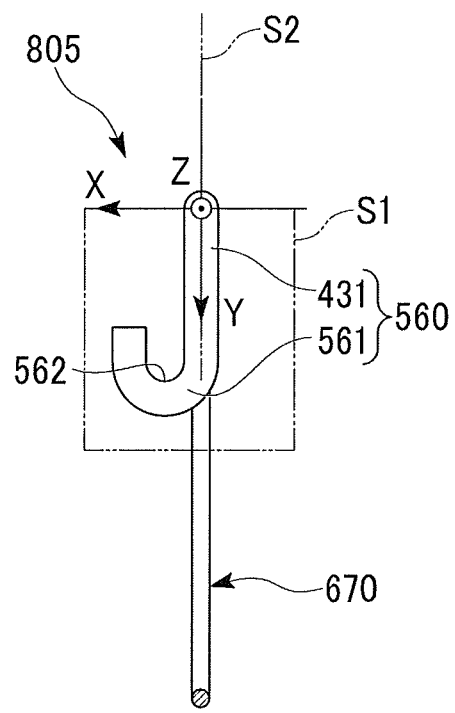
FIG. 51 is a plane view in which a portion of the tissue ligating device according to the eighth embodiment of the present invention is broken out.

As illustrated in FIGS. 50 and 51, a device 805 according to the present embodiment is different only in the direction in which the hook-shaped member 560 is connected to a first end 671 of the suture 670, relative to the device 603 of the sixth embodiment.

The straight portion 431 is orthogonal to the reference line L1 and extends in the positive direction of the Y axis that is parallel to a curved reference plane S2 which becomes a YZ plane. In the present embodiment, the straight portion 431 extends closer to the middle portion of the suture 670 than the ZX plane (disposition reference plane) which is orthogonal to the YZ plane and includes the reference line L1, that is, in the positive direction of the Y axis.

The bent portion 561 is disposed on the reference plane S1, which is an XY plane, in such a way that the groove portion 562 is formed in the positive direction of the X axis with respect to the straight portion 431.

Figure 52:
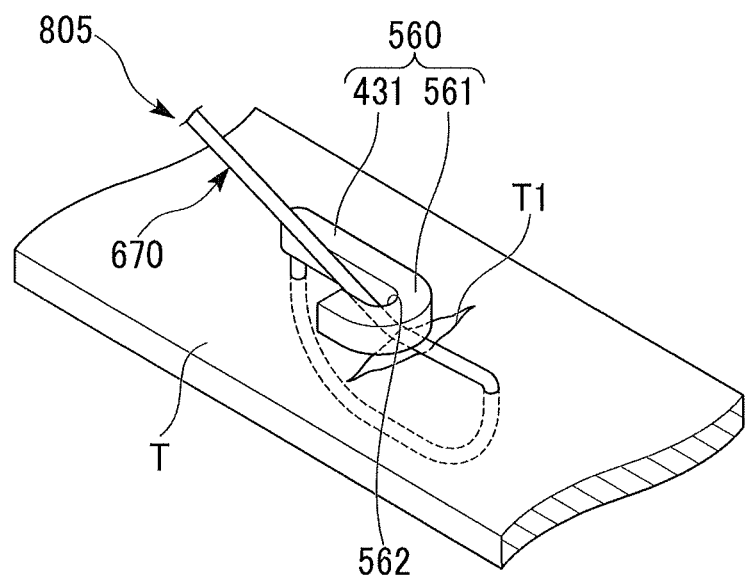
FIG. 52 is a view for describing an operation for suturing a tissue using the tissue ligating device according to the eighth embodiment of the present invention.
Figure 53:
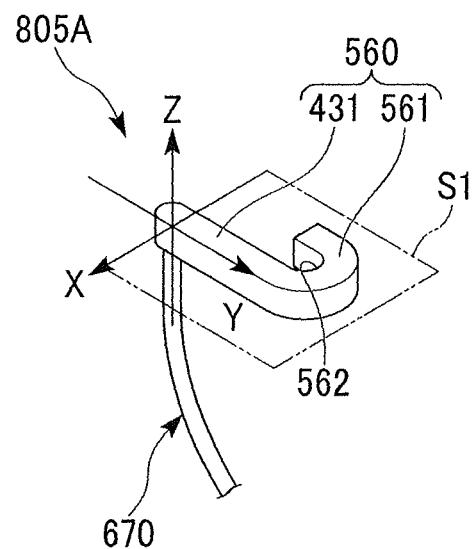
FIG. 53 is a perspective view of major parts of a tissue ligating device according to a modified example of the eighth embodiment of the present invention.
Figure 54:
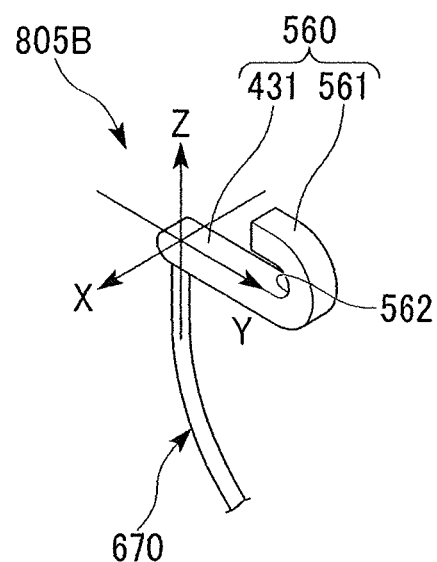
FIG. 54 is a perspective view of the major parts of the tissue ligating device according to the modified example of the eighth embodiment of the present invention.

If the suture 670 is passed through the tissue T so that the hook-shaped member 560 is kept separated from the tissue T, the device 805 configured as above is disposed as shown in FIG. 52.

If the force maintaining the position of the suture 670 is weakened from the state in which a loop is formed by the suture 670 and the suture 670 is disposed between the bent portion 561 and the tissue T, the loop is widened by the elastic restoring force of the suture 670, and the suture 670 is engaged in the groove portion 562 of the bent portion 561.

After this, by following the sequence described with reference to FIG. 35 onward in the sixth embodiment described above, the tissue T is ligated with the suture 670.

As described above, in the device 805 according to the present embodiment, it is possible to engage the suture 670 in the hook-shaped member 560 easily when suturing the tissue T.

Further, because the groove portion 562 is disposed in a side of the positive direction of the Y axis with respect to the first end 671 of the suture 670 and the groove portion 562 is opened toward the first end 671 of the suture 670, it is possible to engage the suture 670 in the groove portion 562 easily using the elastic restoring force of the suture 670.

Further, because the suture 670 is pressed on the inner peripheral surface of the groove portion 562 by the elastic restoring force of the suture 670, it is possible to prevent the suture 670 engaged in the groove portion 562 from easily slipping out of the groove portion 562.

The shape of the device 805 according to the present embodiment may be modified variously.

If the straight portion 431 is extended in the positive direction of the Y axis, the direction in which the bent portion 561 is disposed is not particularly limited. For example, as the device 805A illustrated in FIG. 53, the bent portion 561 may be disposed on the reference plane S1 and the groove portion 562 may be formed in a side of the negative direction of the X axis with respect to the straight portion 431. Further, as the device 805B illustrated in FIG. 54, the bent portion 561 may be disposed on the YZ plane, and the groove portion 562 may be formed in a side of the positive direction of the Z axis with respect to the straight portion 431.

Further, the straight portion 431 may be extended in a direction closer to the positive direction of the Y axis than the ZX plane, even if it is not extended in the positive direction of the Y axis.

Ninth Embodiment

Next, a ninth embodiment of the present invention will be described with reference to FIGS. 55 to 59. The same parts as in the above-mentioned embodiments will be denoted by the same reference numerals, a description thereof will be omitted here, and only differences will be described.

Figure 55:
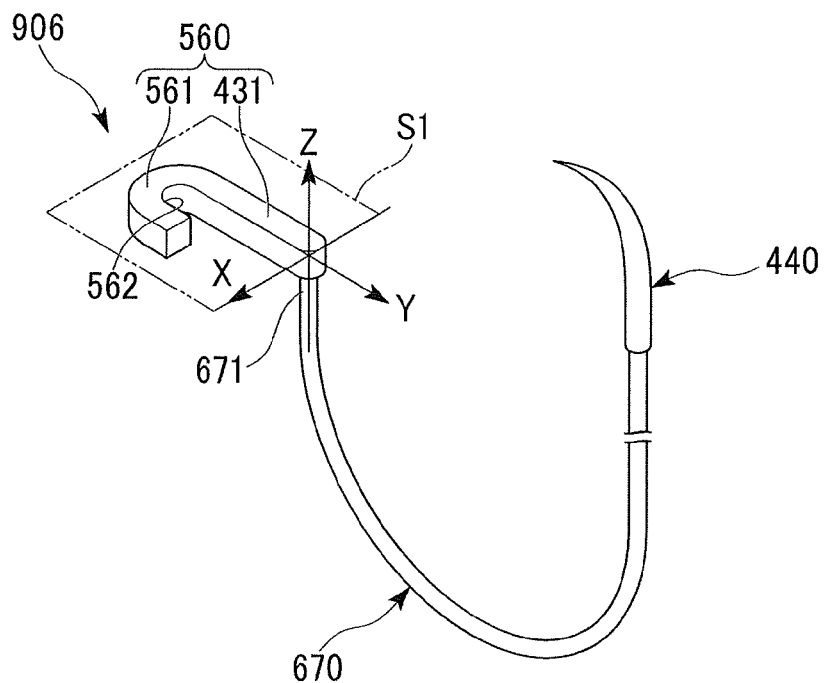
FIG. 55 is a perspective view of a tissue ligating device according to a ninth embodiment of the present invention.
Figure 56:
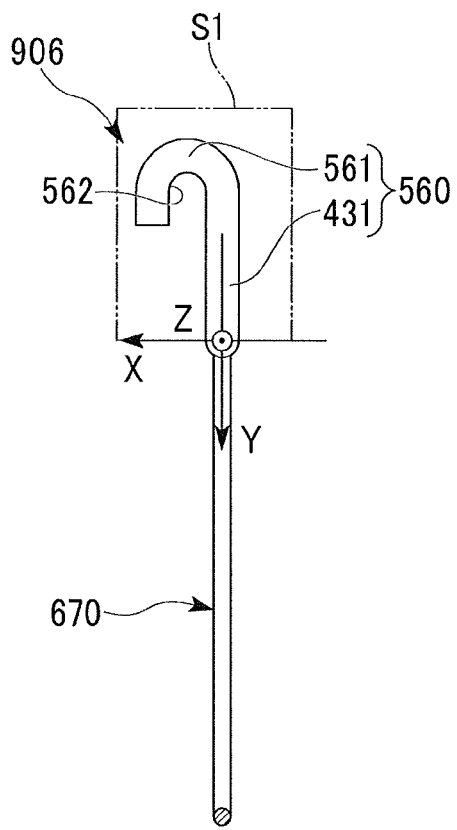
FIG. 56 is a plane view in which a portion of the tissue ligating device according to the ninth embodiment of the present invention is broken out.

As illustrated in FIGS. 55 and 56, a device 906 according to the present embodiment is different only in the direction in which the hook-shaped member 560 is connected to a first end 671 of the suture 670, relative to the device 603A in the modified example of the sixth embodiment.

The straight portion 431 extends in the negative direction of the Y axis, namely in the direction separated from the middle portion of the suture 670.

The bent portion 561 is disposed on the reference plane S1 such that the groove portion 562 is formed in a side of the positive direction of the X axis with respect to the straight portion 431.

Figure 57:
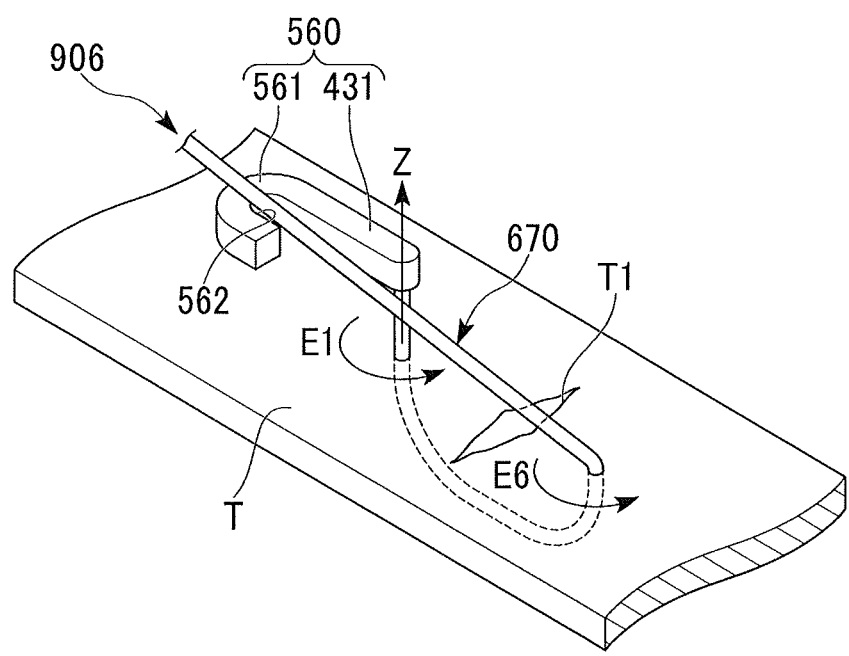
FIG. 57 is a view for describing an operation for suturing a tissue using the tissue ligating device according to the ninth embodiment of the present invention.
Figure 58:
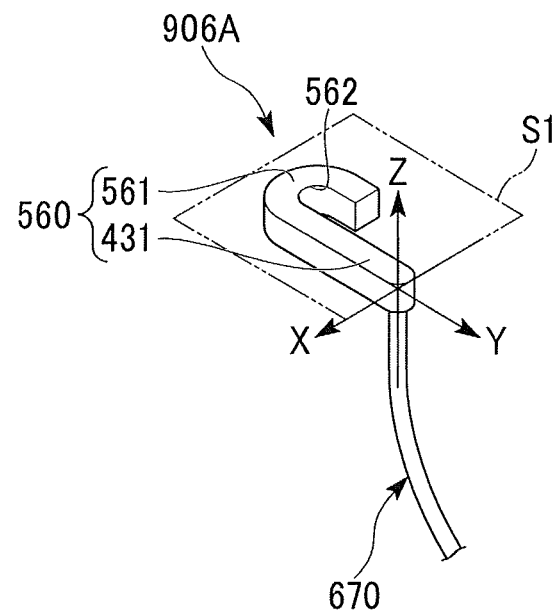
FIG. 58 is a perspective view of major parts of a tissue ligating device according to a modified example of the ninth embodiment of the present invention.
Figure 59:
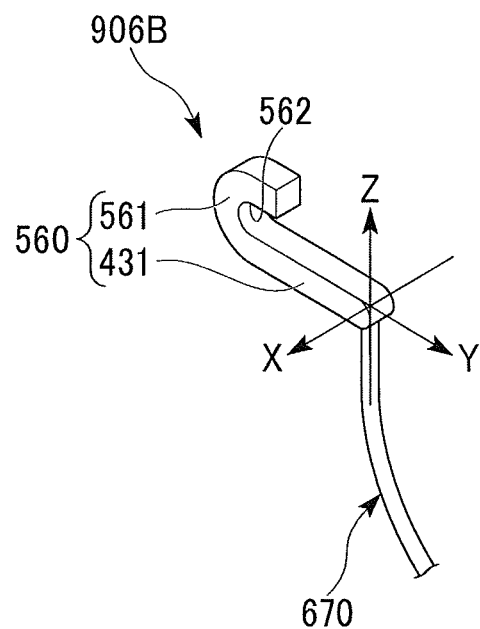
FIG. 59 is a perspective view of the major parts of the tissue ligating device according to the modified example of the ninth embodiment of the present invention.

The device 906 configured as above is disposed as shown in FIG. 57, if the suture 670 is passed through the tissue T and the hook-shaped member 560 is held so as to be floated from the tissue T.

By moving the suture 670 from a place at which the suture 670 protrudes from the tissue T toward the bent portion 561, the suture 670 is engaged in the groove portion 562 of the bent portion 561.

If the suture 670 is rotated in the direction E6 centering on the place protruding from the tissue T, with the suture 670 being engaged in the groove portion 562 of the bent portion 561, the hook-shaped member 560 is rotated around the Z axis about 180 degrees in the direction E1 to become a state as shown in FIG. 44.

After this, by following the sequence described with reference to FIG. 45 onward in the seventh embodiment described above, the tissue T is ligated with the suture 670.

As described above, in the device 906 according to the present embodiment, it is possible to engage the suture 670 in the hook-shaped member 560 easily when suturing the tissue T.

Further, by moving the suture 670 that protrudes from the tissue T toward the bent portion 561, it is possible to engage the suture 670 in the groove portion 562 of the bent portion 561 easily.

The shape of the device 906 according to the present embodiment may be modified variously.

If the straight portion 431 is extended in the negative direction of the Y axis, the direction in which the bent portion 561 is disposed is not particularly limited. For example, as a device 906A illustrated in FIG. 58, the bent portion 561 may be disposed on the reference plane S1 and the groove portion 562 may be formed in a side of the negative direction of the X axis with respect to the straight portion 431. Further, as a device 906B illustrated in FIG. 59, the bent portion 561 may be disposed on the YZ plane, and the groove portion 562 may be formed in a side of the positive direction of the Z axis with respect to the straight portion 431.

Further, the straight portion 431 may be extended in a direction closer to the negative direction of the Y axis than the ZX plane, even if it is not extended in the negative direction of the Y axis.

While the fourth to ninth embodiments of the present invention have been described in detail above with reference to the drawings, a specific configuration is not limited to these embodiments but includes modifications of the configuration within the scope not departing from the spirit of the present invention. Further, the configurations shown in the respective embodiments may be combined suitably.

Figure 60:
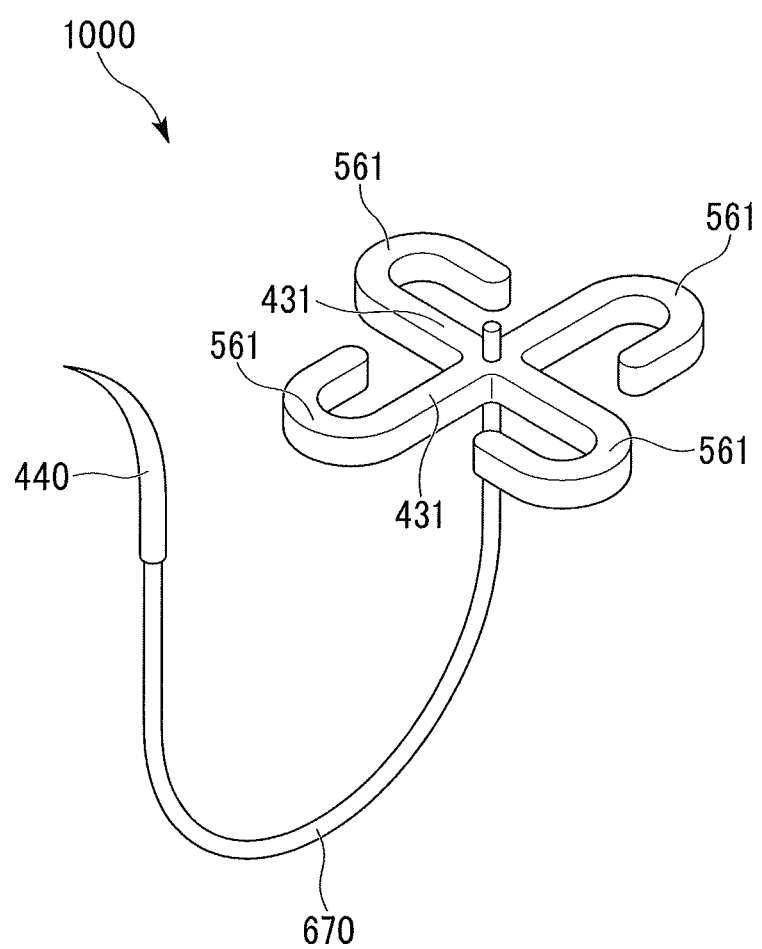
FIG. 60 is a view of a tissue ligating device according to a modified example of an embodiment of the present invention, in which the tissue ligating device according to a combination of the third embodiment to sixth embodiment of the present invention.

For example, a device 1000 illustrated in FIG. 60 in which a hook-shaped member 561 is formed in an end of a suture 670 in four directions from the end of the suture 670 with combination of the configurations according to third embodiment to sixth embodiment.

Figure 61:
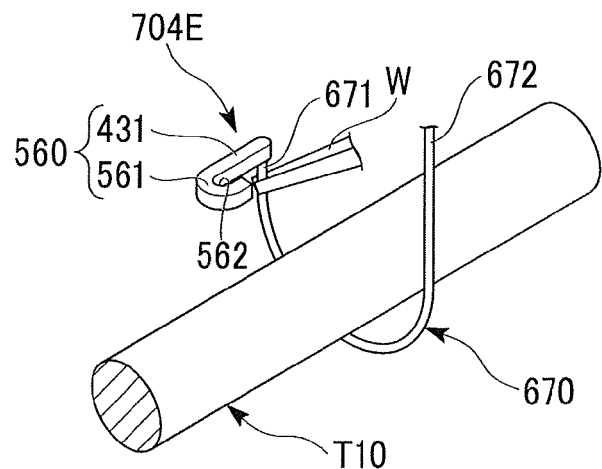
FIG. 61 is a view for describing an operation for suturing a tissue using a tissue ligating device according to the modified example of the embodiment of the present invention.

Further, for example, in the fourth to ninth embodiments, the device may not include a suture needle 440. As such an example, by using the device 704E illustrated in FIG. 61 which is configured without having the suture needle 440 in the device 704 in the above-mentioned embodiments, the case of suturing the blood vessel (the tissue) T10 will be described.

The operator grasps the first end 671 of the suture 670 with the grasping forceps W and disposes the suture 670 so as to encircle the blood vessel T10. Because the suture 670 is formed so as to be bent in the natural state, the suture 670 can be easily disposed so as to encircle the blood vessel T10.

Because the straight portion 431 is extended in the direction orthogonal to a bent reference plane (not shown) on which the suture 670 is bent, the straight portion 431 is disposed so as to be substantially parallel to the blood vessel T10. Meanwhile, in this example, the groove portion 562 of the hook-shaped member 560 is disposed closer to the second end 672 of the suture 670 than the straight portion 431.

Figure 62:
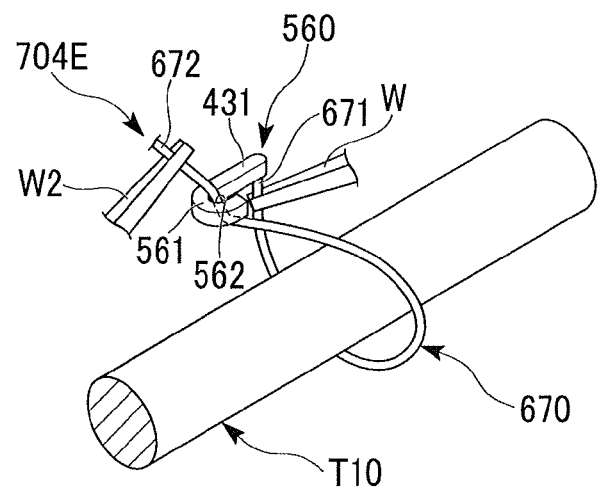
FIG. 62 is a view for describing the operation for suturing the tissue using the tissue ligating device according to the modified example of the embodiment of the present invention.

Next, as illustrated in FIG. 62, with the position toward the first end 671 of the suture 670 being maintained by the grasping forceps W, the second end 672 of the suture 670 is grasped with another grasping forceps W2. When the middle portion of the suture 670 abuts the first end portion of the side connected to the suture 670 of the straight portion 431 and the middle portion of the suture 670 is moved so as to be separated from the first end 671 of the suture 670 along the straight portion 431, the suture 670 is engaged in the groove portion 562.

Figure 63:
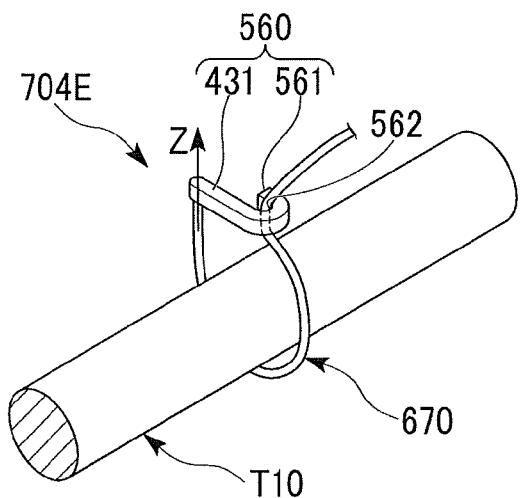
FIG. 63 is a view for describing the operation for suturing the tissue using the tissue ligating device according to the modified example of the embodiment of the present invention.

By releasing the grasping by the grasping forceps W, and pulling the grasping forceps W2 so as to be separated from the blood vessel T10, with the suture 670 engaged in the hook-shaped member 560, the hook-shaped member 560 is rotated around the Z axis about 90 degrees as illustrated in FIG. 63. Further, by pulling the grasping forceps W2, the blood vessel T10 is constricted by the suture 670.

The groove portion 562 is caulked to fix the hook-shaped member 560 to the suture 670, and the blood vessel T10 is ligated.

In the sixth and seventh embodiments, it is assumed that the straight portion 431 is extended in the direction orthogonal to the YZ plane. However, the direction in which the straight portion 431 is extended is not limited thereto, and it may be extended in the direction intersecting the YZ plane.

In the sixth to ninth embodiments, the sutures 670 are formed so as to be bent about 180 degrees at a central angle. However, the central angle of the bent portion in the suture 670 is not limited thereto, and may be any angle as long as it is larger than 0 degrees and smaller than 360 degrees.

In the fourth to ninth embodiments, it is assumed that the hook-shaped member is formed by bending-processing a wire, but the hook-shaped member may be configured by forming the groove portion or the like in a block formed of stainless steel by laser processing, wire-cut processing, or machine processing.

Further, in the fourth to ninth embodiments, it is assumed that the hook-shaped member includes a straight portion, but it may include a wavy portion instead of a straight portion. Further, it may not include a straight portion.

In this case, the first end of the suture is connected to a base portion of the groove portion.

While preferred embodiments of the invention have been described and illustrated above, it should be understood that these are exemplary of the invention and are not to be considered as limiting. Additions, omissions, substitutions, and other modifications are capable of being made without departing from the scope of the present invention. Accordingly, the invention is not to be considered as being limited by the foregoing description, and is only limited by the scope of the appended claims.

What is claimed is:

1. A tissue ligating device for ligating a tissue, comprising:
   a suture having an elastic restoring force, and
   a hook-shaped member including a groove portion, connected to a first end of the suture, and disposed in a direction along a derivation direction of the suture and in a direction opposite to the derivation direction of the suture with respect to the first end of the suture, wherein
   the suture is configured to exert the elastic restoring force having a magnitude sufficient to prevent the hook-shaped member that is connected to the first end of the suture from falling over the tissue under the influence of gravity, and to maintain a state in which the hook-shaped member is separated from the tissue.

2. The tissue ligating device according to claim 1, wherein at least one portion of the suture is formed so as to be bent in a natural state.

3. The tissue ligating device according to claim 2, wherein the groove portion is disposed on an opposite side of the suture with reference to the first end of the suture.

4. The tissue ligating device according to claim 1, wherein a direction facing an opening of the groove portion from a bottom portion of the groove portion faces the first end of the suture.

5. The tissue ligating device according to claim 1, wherein the hook-shaped member includes a straight portion of which a first end portion is connected to the first end of the suture to extend in a straight-line shape,
   the groove portion is formed in a second end portion opposite to the first end portion of the straight portion to which the suture is connected, and
   the straight portion extends in a direction separated from the suture on a reference line, which is a central axis line of the suture through the first end of the suture.

6. The tissue ligating device according to claim 5, wherein the direction facing the opening of the groove portion from the bottom portion of the groove portion becomes substantially parallel to the straight portion, and faces the first end portion of the straight portion to which the suture is connected, and
   an inner wall surface of the groove portion extends to an outer peripheral surface of the straight portion.

7. The tissue ligating device according to claim 5, wherein the straight portion of the hook-shaped member is connected to the suture by coupling the first end of the suture with a fixing portion provided at one end of the straight portion.

8. The tissue ligating device according to claim 1, further comprising a suture needle connected to a second end of the suture.

9. The tissue ligating device according to claim 1, wherein a cross-sectional shape of the hook-shaped member defined by a plane orthogonal to a direction in which the hook-shaped member extends is a rectangular shape.

10. A tissue ligating device for ligating a tissue, comprising:
    a suture having an elastic restoring force, and
    a hook-shaped member including a groove portion, connected to a first end of the suture, and disposed in a direction intersecting a derivation direction of the suture and in a direction opposite to the derivation direction of the suture with respect to the first end of the suture, wherein
    the suture is configured to exert the elastic restoring force having a magnitude sufficient to prevent the hook-shaped member that is connected to the first end of the suture from falling over the tissue under the influence of gravity, and to maintain a state in which the hook-shaped member is separated from the tissue.

11. The tissue ligating device according to claim 10, wherein at least one portion of the suture is formed so as to be bent on a bent reference plane in a natural state.

12. The tissue ligating device according to claim 11, wherein a direction facing an opening of the groove portion from a bottom portion of the groove portion faces a direction intersecting the bent reference plane.

13. The tissue ligating device according to claim 12, wherein the groove portion is disposed at a position closer to a middle portion of the suture than a disposition reference plane which is orthogonal to the bent reference plane and includes a reference line, which is a central axis line of the suture through the first end of the suture.

14. The tissue ligating device according to claim 12, wherein the groove portion is disposed at a position further separated from a middle portion of the suture than the disposition reference plane which is orthogonal to the bent reference plane and includes the reference line, which is the central axis line of the suture through the first end of the suture.

15. The tissue ligating device according to claim 10, wherein the hook-shaped member includes a straight portion of which a first end portion is connected to the first end of the suture to extend in a straight-line shape,
    the groove portion is formed in a second end portion opposite to the first end portion of the straight portion to which the suture is connected, and
    the straight portion extends in a direction intersecting the reference line, which is the central axis line of the suture through the first end of the suture.

16. The tissue ligating device according to claim 15, wherein the direction facing the opening of the groove portion from the bottom portion of the groove portion becomes substantially parallel to the straight portion, and faces the first end portion of the straight portion to which the suture is connected, and
    an inner wall surface of the groove portion extends to an outer peripheral surface of the straight portion.

17. The tissue ligating device according to claim 15, wherein the straight portion of the hook-shaped member is connected to the suture by coupling the first end of the suture with a fixing portion provided at one end of the straight portion.

18. The tissue ligating device according to claim 10, further comprising a suture needle connected to a second end of the suture.

19. The tissue ligating device according to claim 10, wherein a cross-sectional shape of the hook-shaped member defined by a plane orthogonal to a direction in which the hook-shaped member extends is a rectangular shape.

* * * * *